(12) United States Patent
Chain

(10) Patent No.: US 8,173,127 B2
(45) Date of Patent: May 8, 2012

(54) SPECIFIC ANTIBODIES TO AMYLOID BETA PEPTIDE, PHARMACEUTICAL COMPOSITIONS AND METHODS OF USE THEREOF

(75) Inventor: Daniel G. Chain, New York, NY (US)

(73) Assignee: Intellect Neurosciences, Inc., New York, NC (US)

( * ) Notice: Subject to any disclaimer, the term of this patent is extended or adjusted under 35 U.S.C. 154(b) by 6 days.

(21) Appl. No.: 10/084,380

(22) Filed: Feb. 28, 2002

(65) Prior Publication Data

US 2003/0073655 A1  Apr. 17, 2003

Related U.S. Application Data

(63) Continuation-in-part of application No. 09/402,820, filed as application No. PCT/US98/06900 on Apr. 9, 1998, now abandoned.

(60) Provisional application No. 60/041,850, filed on Apr. 9, 1997.

(51) Int. Cl.
  *A61K 39/395* (2006.01)
  *A61K 48/00* (2006.01)

(52) U.S. Cl. .............. 424/135.1; 424/133.1; 424/139.1; 424/141.1; 424/172.1; 514/44 R

(58) Field of Classification Search .................... 514/44; 424/130.1, 132.1, 133.1, 136.1, 141.1, 142.1
  See application file for complete search history.

(56) References Cited

U.S. PATENT DOCUMENTS

| | | | |
|---|---|---|---|
| 4,741,901 A | 5/1988 | Levinson et al. | |
| 5,231,000 A | 7/1993 | Majocha et al. | |
| 5,441,870 A | 8/1995 | Seubert et al. | |
| 5,589,154 A | 12/1996 | Anderson | |
| 5,593,846 A | 1/1997 | Schenk et al. | |
| 5,604,102 A | 2/1997 | McConlogue et al. | |
| 5,688,651 A | 11/1997 | Solomon | |
| 5,721,130 A | 2/1998 | Seubert et al. | |
| 5,750,349 A * | 5/1998 | Suzuki et al. | 435/7.1 |
| 5,786,180 A * | 7/1998 | Konig et al. | 435/70.21 |
| 5,851,996 A | 12/1998 | Kline | |
| 5,965,614 A * | 10/1999 | Audia et al. | 514/538 |
| 6,114,133 A | 9/2000 | Seubert et al. | |
| 6,180,370 B1 | 1/2001 | Queen et al. | |
| 6,287,793 B1 | 9/2001 | Schenk et al. | |
| 6,610,493 B1 | 8/2003 | Citron et al. | |
| 6,710,226 B1 | 3/2004 | Schenk | |
| 6,717,031 B2 | 4/2004 | Games et al. | |
| 6,743,427 B1 | 6/2004 | Schenk | |
| 6,761,888 B1 | 7/2004 | Schenk | |
| 6,787,523 B1 | 9/2004 | Schenk | |
| 6,787,637 B1 * | 9/2004 | Schenk | 530/387.1 |
| 6,905,686 B1 | 6/2005 | Schenk | |
| 6,913,745 B1 | 7/2005 | Schenk | |
| 6,923,964 B1 | 8/2005 | Schenk | |

FOREIGN PATENT DOCUMENTS

| | | | |
|---|---|---|---|
| EP | 0613007 A2 * | 2/1994 | |
| EP | 0 683 234 | 11/1995 | |
| EP | 2006303 | 12/2008 | |
| EP | 1200476 B1 | 5/2009 | |
| WO | WO 89/01975 | 3/1989 | |
| WO | WO 94/25585 | 11/1994 | |
| WO | WO 96/18900 | 6/1996 | |
| WO | WO 96/25435 A1 | 8/1996 | |
| WO | WO 98/44955 | 10/1998 | |
| WO | WO 99/27944 | * 6/1999 | |
| WO | 00/72876 | * 12/2000 | |
| WO | WO-03/074081 | 9/2003 | |

OTHER PUBLICATIONS

Bard F et al. Peripherally administered antibodies against amyloid beta-peptide enter the central nervous system and reduce pathology in a mouse model of Alzheimer disease. Nature Medicine, 6(8): 916-919, 2000.*
Solomon B et al. Disaggregation of Alzheimer beta-amyloid by site-directed mAb. Proc Natl Acad Sci, USA, 94: 4109-4112, 1997.*
Saido T et al. Amino—and carboxyl-terminal heterogeneity of beta-amyloid peptides deposited in human brain. Neurosci Lett, 215: 173-176, 1996.*
Harigaya Y et al. Amyloid beta protein starting pyroglutamate at position 3 is a major component of the amyloid deposits in the Alzheimer's disease brain. Biochem Biophys Res Comm. 276: 422-427, 2000.*
Frenkel D et al. N-terminal EFRH sequence of Alzheimer's b-amyloid peptide represents the epitope of its anti-aggregating antibodies. J Neuroimmunol, 88: 85-90, 1998.*
Su Y and Ni B. Selective deposition of amyloid-beta protein in the entorhinal-dentate projection of a transgenic mouse model of Alzheimer's disease. J Neurosci Res, 53: 177-186, 1998.*
Buxbaum JN. Treatment and prevention of the amyloidoses: Can the lessons learned by applied to sporadic inclusion-body myositis? Neurology, 66(Suppl 1): S110-S113, 2006.*
Verma. Gene therapy—promises, problems and prospects. Nature. Sep. 18, 1997;389(6648):239-42.*
Philips. The challenge of gene therapy and DNA delivery. J Pharm Pharmacol. Sep. 2001;53(9):1169-74.*
Mak et al. Polyclonals to beta-amyloid(1-42) identify most plaque and vascular deposits in Alzheimer cortex, but not striatum. Brain Res. Dec. 19, 1994;667(1):138-42.*
Piccioli 1995 (Neuron 15:373-384).*
Duenas et al, *Bio Techniques*, 16(3):476-482 (1994).
Goding, *Monoclonal Antibodies*, Academic Press Inc., London, pp. 56-97 (1983).

(Continued)

Primary Examiner — Daniel E Kolker
(74) Attorney, Agent, or Firm — Fish & Richardson P.C.

(57) ABSTRACT

The invention relates to methods of treating a subject having Alzheimer's Disease, comprising the step of administering an antibody molecule which is targeted to β amyloid peptide or to fragment thereof. In another embodiment the invention relates to methods of treating a disease or a disorder, characterized by amyloid beta deposition. In another embodiment, the invention relates to an antibody molecule, which is free end-specific for the N-terminus or the C-terminus of an amyloid β peptide and to a pharmaceutical composition thereof. In another embodiment, the invention relates to an antibody molecule, which is targeted to the free C or N-terminus of a N-and/or C-terminus truncated amyloid β peptide fragment.

23 Claims, 7 Drawing Sheets

OTHER PUBLICATIONS

Jarrett et al, "The carboxy terminus of the beta amyloid protein is critical for the seeding of amyloid formation: implications for the pathogenesis of Alzheimer's disease," *Biochemistry* 32:4693-4697 (1993).

Quitschke et al., "The initator element and proximal upstream sequences affect transcriptional activity and start site selection in the amyloid β-protein precursor promoter," *J. Biol. Chem.* 271(36), pp. 22231-22239 (1996).

Saido et al., "Autolytic transition of μ-calpain upon activation as resolved by antibodies distinguishing between the pre- and post-autolysis forms," *J. Biochem.* 111:81-86 (1992).

Saido et al., "In situ capture of mu-calpain activation in platelets," *J. Biol. Chem.* 268(10): (1993) (Abstract Only).

Saido et al., "Spatial resolution of the primary β-amyloidogenic process induced in postischemic hippocampus," *J. Biol. Chem.* 269(21):15253-15257 (1994).

Bacskai, B.J. et al. "Imaging of Amyloid-Beta Deposits in Brains of Living Mice Permits Direct Observation of Clearance of Plaques With Immunotherapy." Nature Medicine, Mar. 2001, vol. 7, No. 3, pp. 369-372.

Frenkel, Dan et al. "Modulation of Alzheimer's Beta-Amyloid Neurotoxicity by Site-Directed Single Chain Antibody." Journal of Neuroimmunology, Vo. 160, No. 1-2, Jul. 2000, pp. 23-31.

Solomon, B., Immunological Concept in the Treatment of Alzheimer's Disease, *Drug Dev. Res.* 56:163-167 (2002).

Solomon, B., Immunotherapeutic Strategies for Prevention and Treatment of Alzheimer's Disease, *DNA and Cell Biol.* 20:697-703 (2001).

Abbas, et al., Cellular and Molecular Biology, WB Saunders Company, 1991. Page 52.

Van Engelen et al., Immunoglobulin treatment in human and experimental epilepsy. J. Neurol. Neurosurg. Psychiatry, 1994, 57(Suppl.):72-75.

Wurster et al., Passage of intravenous immunoglobulin and interaction with the CNS. J. Neurol. Neurosurg. Psychiatry, 1994, 57(Suppl.):21-25.

Zalutzky et al., Monoclonal Antibody and F(ab$^{41}$)$_2$ Fragment Delivery to Tumor in Patients with Glioma: Comparison of Intracarotid and Intravenous Administration. Cancer Research, 1990, 50:4105-4110.

Notice of Opposition to European Patent No. 0994728, filed Apr. 30, 2009 (15 pages).

Opponent's Translation of Petition submitted Sep. 16, 2005 on behalf of Intellect Neurosciences during appeal proceedings of Japanese application 10-543043 (17 pages).

Anderson et al., Exact cleavage site of Alzheimer amyloid precursor in neuronal PC-12 Cells, Neuroscience Letters (1991) 128:126-128.

Citron et al., Evidence that the 42-amino and 40-amino acid forms of amyloid β protein are generated from the β-amyloid precursor protein by different protease activities, Proc. Natl. Acad. Sci. USA (1996) 93:13170-13175.

Kim et al., Production and Characterization of Monoclonal Antibodies Reactive to Synthetic Cerebrovascular Amyloid Peptide, Neuroscience Research Communications (1988) No. 3, 2:121-130.

Li et al., An Atomic Model for the Pleated β-Sheet Structure of Aβ Amyloid Protofilaments, Biophysical Journal, (1999) 76:2871-2878.

Petkova et al., A structural model for Alzheimer's β-amyloid fibrils based on experimental constraints from solid state NMR, PNAS (2002) 99:16742-16747.

Soto and Castano, The Conformation of Alzheimer's β peptide determines the rate of amyloid formation and its resistance to proteolysis, Biochem. J. (1996) 314:701-707.

Allsop et al., Immunohistochemical evidence for the derivation of a peptide ligand from the amyloid beta-protein precursor of Alzheimer disease, Proc. Natl. Acad. Sci. USA, 1988, 85:2790-4.

Baldwin et al., Are denatured proteins ever random coils?, Proc. Natl. Acad. Sci. USA, 2000, 97:12391-12392.

Bancher et al Immunoreactivity of Neuronal Lipofuscin With Monoclonal Antibodies to the Amyloid β-Protein, Neurobiol. Aging, 1989, 10:125-32.

Kanemaru et al., The presence of a novel protein in calf serum that recognizes beta amyloid in the formalin-fixed section, Am. J. Pathol., 1990, 137:677-87.

Laver et al., Epitopes on Protein Antigens: Misconceptions and Realities, Cell, 1990, 61:553-556.

Morgan, D., Immunotherapy for Alzheimer's Disease, J. Intern. Med. 2011; 269:54-63.

Saitoh et al., Immunological analysis of Alzheimer's disease using anti-protein monoclonal antibodies, Sapporo Medical J, 1991,60:309-20. (Japanese language article with English language Abstract).

Seubert et al., Isolation and quantification of soluble Alzheimer's beta-peptide from biological fluids, Nature, 1992, 359:325-327.

Solomon et al., Disaggregation of Alzheimer β-amyloid by site-directed mAb, Proc. Natl. Acad. Sci. USA, 1997, 94:4109-4112.

Tamaoka et al., Amyloid β protein 42(43) in cerebrospinal fluid of patients with Alzheimer's disease, J. Neurol. Sci., 1997, 148:41-45.

Cotman, C.W., The β-amyloid peptide, peptide self-assembly, and the emergence of biological activities: a new principle in peptide function and the induction of neuropathology, Annals NY Acad Sci, vol. 814, pp. 1-816, 1997.

Behl, C., Amyloid β-protein toxicity and oxidative stress in Alzheimer's disease, Cell Tissue Res, vol. 290, pp. 471-480, 1997.

Page downloaded Oct. 27, 2011 from website "Alzheimer Research Forum" at www.alzforum.org/res/com/ant/default.asp after searching for "3D6 and Johnson-Wood".

Provisional and non-binding opinion of the Opposition Division dated Nov. 12, 2010, issued by the European Patent Office in connection with opposition filed against European Patent No. 0 994 728, which issued from counterpart application EP 98918035.1, 5 pages.

Minutes of Oral Proceedings before the Opposition Division held on Jul. 1, 2011, in connection with opposition filed against European Patent No. 0 994 728, which issued from counterpart application EP 98918035.1; dated Jul. 26, 2011, 4 pages.

Decision revoking the European Patent, dated Oct. 7, 2011, issued by the European Patent Office in connection with opposition filed against European Patent No. 0 994 728, which issued from counterpart application EP 98918035.1, 26 pages.

Ito et al., Cerebral clearance of human amyloid-β peptide (1-40) across the blood-brain barrier is reduced by selfaggregation and formation of low-density lipoprotein receptor-related protein-1 ligand complexes, J Neurochemistry, vol. 103, pp. 2482-2490, 2007.

Declaration of Dr. K. Rock, dated Apr. 28, 2011, filed in connection with opposition filed against European Patent No. 0 994 728, which issued from counterpart application EP 98918035.1, 8 pages.

The American Heritage Dictionary, 3rd Edition, p. 1953.

Immunobiology, 6th Edition, p. 688.

Fundamental Immunology, 6th Edition, pp. 170-171.

Van Regenmortel, M., J. Immunological Methods, vol. 216, pp. 37-48, 1998.

Busciglio J, et al, (1193) "Generation of b-amyloid in the secretory pathway in neuronal and nonneuronal cells" Proc. Natl. Acad. Sci. 90, 2092-2096.

Gegeddes JW et al. (1999) "N-terminus truncated b-amyloid peptides and C-terminus truncated secreted forms of of anyloid precursor protein: distinct roles in the pathogenesis of Alzheimer's disease" Neuobiol of Aging 20, 75-79.

Haas C et al. (1992) "Amyloid b-peptide is produced by cultured cells during normal metabolism" Nature 359, 322-325.

Haas C et al. (1993)"Cellular processing of β amyloid precursor protein and the genesis of amyloid β-peptide." Cell 75, <1039-1042.

Higgins LS et al. (1996) "p3 b amyloid peptide has a unique and potentially pathogenic immunohistochemical profile in Alzheimer's disease brain." Am. J. Pathol 149, 585-596.

Johnson-Wood K. et al. "Amyloid precursor protein processing and A beta42 deposition in a transfenic mouse model of Alzheimer disease" Proc Natl. Acad. Sci U.S.A. Feb 18, 1997;94 (4): 1550-5.

Lalowski M (1996) "The nonamyloidogenic p3 fragment (amyloid β 17-42) is a major constituent of Down's syndrome cerebeller preamyloid." J Biol Chem 271, 33623-31.

Larner AJ (1999) "Hypothesis: amyloid b peptides truncated at the N-terminus contribute to the pathogenesis of Alzheimer's disease." Neurbiol. Of Aging 20, 65-69.

Masters CL et al. (1985) "Amyloid plaque core protein in Alzheimer's disease and Down syndrome." *Proc. Natl. Acad. Sci.* 82, 4245-9.

Miller DL et al. (1994) "Peptide compositions of the cerebrovascular and senile plaque core amyloid deposits of Alzheimer's disease." Archives of Biochemistry and Biophysics 301, 41-52.

Naslund et al. (1994) "Relative abundance of Alzheimer aβ amyloid peptide variants in Alzheimer disease and normal aging." Proc. Natl. Acad. Sci. USA 91, 8378-8382.

Pike CJ et al. (1995) "Amino-terminal deletions enhance aggregation of β-amyloid peptides in vitro." J Biol Chem 270, 23895-8.

Seubert et al. (1992) "Isolation and quantification of soluble Alzheimer's β-peptide from biological fluids." Nature 359, 325-327.

Vigo-Pelfrey C et al. (1993) "Characterization of beta-amyloid peptide from human cerebrospinal fluid." J Neurochem 61, 1965-8.

Hanan, Eilat at al., "Inhibitory effect of monoclonal antibodies on Alzheimer's Beta-amyloid peptide aggregation" Int. J. Exp. Clin. Invest., vol. 3, pp. 130-133 (1996).

Solomon, Beka et al., "Monoclonal antibodies inhibit in vitro fibrillar aggregation of the Alzheimer Betaamyloid peptide", Proc. Natl. Acad. Sci. USA, vol. 93, pp. 452-455 (1996).

Solomon, Beka et al., "Disaggregation of Alzheimer Beta-amyloid by site-directed mAb.", Proc. Natl. Acad. Sci. USA, vol. 94, pp. 4109-4112 (1997).

Tsuzuki et al., "amyloid beta protein in rot soleus muscle in chloroquine-induced myopathy using end-specific antibodies for A beta 40 and A beta 42: immunohistochemical evidence for amyloid beta protein", *Neurosci Letters* 202 (1-2):77-80(1995).

Turner et al., "Mayloids β40 and β42 Are Generated Intracellularly in Cultured Human Neurons and Their Secretion Increases with maturation", *J Biol Chem* 271 (15):8966:8970 (1996).

Yanagisawa et al., "Fractionation of Amyloid β protein (Aβ) in Alzheimer's Disease and Down's Syndrome Brains: Presence of Membrane-Bound Aβ", *Ann NY Acad Sci* 786:184-194 (1996).

Gravina et al., "Amyloid β Protein (Aβ) in Alzheimer's Disease Brain: Biochemical and Immunocytochemical Analysis with Antibodies Specific for Forms Ending at Aβ40 or Aβ42(43)", J boil Chem 270 (13): 7013-7016 (1995).

Harrington et al.,"Characterisation of an epitome specific to the neuron-specific isoform of human enolase recognized by a monoclonal antibody raised against a synthetic peptide corresponding to the C-terminus of β/A-protein", *Biochim Bioohys Acta* 1158:120-127 (1993).

Higgins et al., "Transgenic Mouse Brain Histophathology Resembles Early Alzheimer's Disease", *Ann Neurol* 35:598-607 (1994).

Iwatsubo et al., Visualization of Aβ42 (43) and Aβ40 in Senile Plaques with End-Specific Aβ Monoclonals: Evidence that an Initally Depsoited specids is Aβ42(43) *Neuron* 13:45-53 (1994).

Iwatsubo et al., "Amyloid β protein (Aβ) Deposition: Aβ42 (43) Precedes Aβ40 in Down Syndrome". *Ann Neurol* 37:294-299 (1995).

Konig et al., "Development and Characterization of a Monoclonal Antibody 369. 2B Specific for the Carboxyl-Terminus of the βA4 Peptide", *Ann NY Acad Sci* 777:345-355 (1996).

Mann et al., "The extent of amyloid deposition in brain in patients with Down's Syndrome does not depend upon the apolipoprotein E genotype", *Neurosci Letters* 196 (1-2):105-108 (1995).

Mann et al., "Predominant Deposition of Amyloid β42 (43) in Plaques in Cases of Alzheimer's Disease and Hereditary Cerebral Hemorrhage Associated with Mutations in the Amyloid Precursor Protein Gene", *Am J Pathol* 148 (4):1257-1265 (1996).

Mann et al., Amyloid beta protein (Abeta) deposition in chromosome 14-linked Alzheimer's diseas: predominance of Abeta 43 (43) *Ann Neurol* 40 (2):149-156 (1996).

Murphy et al., "Development of a Monoclonal Antibody Specific for the COOH-Terminal of β-Amyloid 1-42 and Its Immunohistochemical reactivity in Alzheimer's Disease and Related Disorders", *Am J Pathol* 144 (5):1082-1088 (1994).

Nakamura et al., "Carboxyl end-specific monoclonal antibodies to amyloid beta protein (A beta) subtypes (A beta 40 and A beta 42 (43) differentiate A beta in senile plaques and amyloid angiopathy in brains of aged cynomolgus monkeys." *Neurosci Letters* 201(2):151-154 (1996).

Saido et al., "Spatial Resolution of Fodrin Proteolysis in Postischemic Brain", *J Biol Chem* 268(33): 25239-25243 (1993).

Suzuki et al., "High Tissue Content of Soluble β1-40 is Linked to Cerebral Amyloid Angiopathy", *Am J Pathol* 145 (2): 452-460 (1994).

Tamaoka et al., "Amyloid β protein 1-42/43 (Aβ 1-42/43) in cerebellar diffuse plaques: Enzyme-linked immunosorbent assay and immunocytochemical study", *Brain Res* 679:151-156 (1995).

Duenas et al. Bio Techniques, 16 (3): 476-472, (1994).

Johnson-Wood K. et al, "Amyloid precursor protein processing and A beta42 deposition in a transgenic mouse model of Alzheimer disease," 1997, Proc Natl Acad Sci U S A Feb 18;94(4), pp. 1550-1555.

* cited by examiner

SPECIFIC ANTIBODIES TO AMYLOID BETA PEPTIDE, PHARMACEUTICAL COMPOSITIONS AND METHODS OF USE THEREOF

CROSS REFERENCE TO PRIOR APPLICATIONS

This application is a Continuation-in Part of U.S. Ser. No. 09/402,820, filed Oct. 12, 1999, which is a U.S. National phase application under 35 U.S.C. §371 of International Patent Application No. PCT/US/98/06900, filed Apr. 9, 1998, which claim priority from provisional Application No. 60/041,850, filed Apr. 9, 1997, which are incorporated herein by reference.

FIELD OF THE INVENTION

The invention relates to methods of treating a subject having Alzheimer's Disease, comprising the step of administering an antibody molecule which is targeted to β amyloid peptide or to fragment thereof. In another embodiment the invention relates to methods of treating a disease or a disorder, characterized by amyloid beta deposition. In another embodiment, the invention relates to an antibody molecule, which is free end-specific for the N-terminus or the C-terminus of an amyloid β peptide, or fragment thereof, and to a pharmaceutical composition thereof.

BACKGROUND OF THE INVENTION

A major histopathological hallmark of Alzheimer's Diseae (AD) is the presence of amyloid deposits within neuritic and difuse plaques in the parenchyma of the amygdala, hippocampus and neocortex (Glenner and Wong, 1984; Masters et al., 1985; Sisodia and Price, 1995). Amyloid is a generic tern that describes fibrillar aggregates that have a common β-pleated structure. These aggregates exhibit birefringent properties in He presence of Congo red and polarized light (Glenner and Wong, 1984). The diffuse plaque is thought to be relatively benign in contrast to the neuritic plaque which appears to be strongly correlated with reactive and degenerative processes (Dickson et al., 1988; Tagliavini et al., 1988; Yamaguchi et al., 1989; Yamaguchi et al., 1992). One of the principal components of neuritic plaques is a 42 amino acid residue amyloid-β (Aβ) peptide (Miller et al., 1993; Roher et al., 1993) that is derived from the much larger β-amyloid precursor protein, β APP (or APP) (Kang et al., 1987). Aβ 1-42 is produced less abundantly than the 1-40 Aβ peptide (Haass et al., 1992; Seubert et al., 1992), but the preferential deposition of Aβ 1-42 results from the fact that this COOH-extended form is more insoluble than 1-40 Aβ and is more prone to aggregate and form anti-parallel β-pleated sheets (Joachim et al., 1989; Halverson et al., 1990; Barrow et al., 1992; Burdick et al., 1992; Fabian et al., 1994). Aβ 1-42 can seed the aggregation of Aβ 1-40 (Jarrett and Lansbury 1993).

The APP gene was sequenced and found to be encoded on chromosome 21 (Kang al., 1987). Expression of the APP gene generates several Aβ-containing isoforms of 695, 751 and 770 amino acids, with the latter two APPs containing a domain that shares structural and functional homologies with Kunitz serene protease inhibitors (Kang et al., 1987; Kitaguchi et al., 1988; Polite et al., 1988; Tanzi et al., 1988; Konig et al., 1992). The functions of APP in the nervous system remain to be defined, although there is increasing evidence that APP has a role in mediating adhesion and growth of neurons (Schubert et al., 1989; Saitoh et al., 1994; Roch, 1995) and possibly in a G protein-linked signal transduction pathway (Nishimoto et al., 1993). In cultured cells, APPs mature through the constitutive secretory pathway (Weidemann et al., 1989; Haass et al., 1992; Sisodia 1992) and some cell-surface-bound APPs are cleaved within the Aβ domain by an enzyme, designated α-secretase, (Esch et al., 1990), an event that precludes Aβ amyloidogenesis. Several studies have delineated two additional pathways of APP processing that are both amyloidogenic: first an endosomal/lysosomal pathway generates a complex set of APP-related membrane-bound fragments, some of which contain the entire Aβ sequence (Haass et al., 1992; Golde et al., 1992); and second, by mechanisms that are not fully understood, Aβ 1-40 is secreted into the conditioned medium and is present in cerebrospinal fluid in vivo (Haass et al., 1992; Seubert et al., 1992; Shoji et al., 1992; Busciglio et al., 1993). Lysosomal degradation is no longer thought to contribute significantly to the production of Aβ (Sisodia and Price 1995). The proteolytic enzymes responsible for the cleavages at the NH2 and COOH termini of Aβ are termed β (BACE) and γ secretase, respectively. Until recently, it was generally believed that Aβ is generated by aberrant metabolism of the precursor. The presence, however, of Aβ in conditioned medium of a wide variety of cells in culture and in human cerebrospinal fluid suggest that Aβ is produced as a normal function of cells.

The main focus of researchers and the principal aim of those associated with drug development for AD is to reduce the amount of Aβ deposits in the central nervous system (CNS). These activities fall into several general areas: factors affecting the production of Aβ, the clearance of Aβ, and preventing the formation of insoluble Aβ fibrils. Another therapeutic goal is to reduce inflammatory responses evoked by Aβ neurotoxicity.

Given that neurotoxicity appears to be associated with β-pleated aggregates of Aβ, one therapeutic approach is to inhibit or retard Aβ-aggregation. The advantage of this approach is that the intracellular mechanisms triggering the overproduction of Aβ or the effects induced intracellularly by Aβ need not be well understood. Various agents that bind to Aβ are capable of inhibiting Aβ neurotoxicity in vitro, for example, the Aβ-binding dye, Congo Red, completely inhibits Aβ-induced toxicity in cultured neurons (Yankner et al., 1995). Similarly, the antibiotic rifampacin also prevents Aβ aggregation and subsequent neurotoxicity (Tomiyama et al., 1994). Other compounds are under development as inhibitors of this process either by binding Aβ directly, e.g., hexadecyl-N-methylpiperidinium HMP) bromide (Wood et al., 1996), or by preventing the interaction of Aβ with other molecules that contribute to the formation of Aβ deposition. An example of such a molecule is heparan sulfate or the heparan sulfate proteoglycan, perlecan, which has been identified in all amyloids and is implicated in the earliest stages of inflammation associated amyloid induction.

Heparan sulfate interacts with the Aβ peptide and imparts characteristic secondary and tertiary amyloid structural features. Recently, small molecule anionic sulfates have been shown to interfere with this reaction to prevent or arrest amyloidogenesis (Kisilevsky, 199S), although it is not evident whether these compounds will enter the CNS. A peptide based on the sequence of the perlecan-binding domain appears to inhibit the interaction between Aβ and perlecan, and the ability of Aβ-derived peptides to inhibit self-polymerization is being explored as a potential lead to developing therapeutic treatments for AD. The effectiveness of these compounds in vivo, however, is likely to be modest for a number of reasons, most notably the need for chronic penetration of the blood brain barrier.

An alternative to a peptide-based approach is to elucidate the cellular mechanism of Aβ neurotoxicity and develop therapeutics aimed at those cellular targets. The focus has been on controlling calcium dysfunction of free radical mediated neuronal damage. It has been postulated that Aβ binds to RAGE (the receptor for advanced glycation end-products) on the cell surface, thereby triggering reactions that could generate cytotoxic oxidizing stimuli (Yan et al., 1996). Blocking access of Aβ to the cell surface biding site(s) might retard progression of neuronal damage in AD. To date there are no specific pharmacological agents for blocking Aβ-induced neurotoxicity.

SUMMARY OF THE INVENTION

The invention relates to methods of treating a subject having Alzheimer's Disease or another disease or disorder characterized by amyloid β deposition, comprising the step of administering an antibody molecule which is targeted to β amyloid peptide or to fragment thereof. In another embodiment, the invention relates to an antibody molecule, which is free end-specific for the N-terminus or the C-terminus of an amyloid β peptide aad to a pharmaceutical composition thereof. In another embodiment, the invention relates to an antibody molecule, which is targeted to the free C or N-terminus of N-and/or C-terminus truncated amyloid β peptide fragment.

In one embodiment the invention relates to a method of treating a subject having Alzheimer's Disease, comprising the step of administering an antibody which is targeted to amyloid βpeptide, or to fragment thereof thereby treating the subject having Alzheimer's Disease.

In one embodiment the invention relates to a method of treating a subject having a disease or disorder characterized by amyloid β deposition, comprising tie step of administering an antibody which is targeted to amyloid β peptide, or to fragment thereof thereby treating the subject having a disease or disorder characterized by amyloid β deposition. Examples of such disorders include: mild cognitive impairment (MCI), cerebral amyloid angiopathy or congiophylic angiopathy, Down Syndrome-associated Alzheimer's disease, and inclusion-body myositis.

In another embodiment the invention relates to a method for delaying or inhibiting or suppressing the accumulation of an amyloid β peptide or fragment thereof, comprising the step of administering an antibody which is targeted to an amyloid β peptide, or to fragment thereof, thereby delaying or inhibiting or suppressing accumulation of amyloid β peptide or fragment thereof in the brain.

In another embodiment the invention relates to a method for delaying or inhibiting or suppressing the neurotoxicity of amyloid β peptide or fragment thereof, comprising the step of administering an antibody which is targeted to amyloid β peptide, or fragment thereof, thereby delaying or inhibiting or suppressing the neurotoxicity of amyloid β peptide or fragment thereof.

In another embodiment the invention relates to an antibody that is free-end specific and is targeted to the free N-terminus of amyloid β-peptide.

In another embodiment the invention relates to an antibody that is free-end specific and is targeted to the free N-terminus of amyloid β-peptide, wherein the first amino acid of the free N-terminus of amyloid β-peptide is aspartate In another embodiment the invention relates to an antibody that is free-end specific and is targeted to the free N terminus of N- and/or C-terminus-truncated amyloid β peptide fragment.

In another embodiment the invention relates to an antibody that is free-end specific and is targeted to the free C-terminus of the amyloid β-peptide Aβ1-39, Aβ1-40, Aβ1-41, or Aβ1-43.

In another embodiment the invention relates to an antibody that is free-end specific and is targeted to the free C-terminus of N- and/or C-terminus-truncated amyloid β peptide fragment.

In another embodiment the invention relates to a single chain antibody that is free-end specific and is targeted to the free C-terminus of the amyloid β-peptide Aβ1-42.

Another object of the invention is to provide a method whereby cells of the nervous system are conferred with the ability to ectopically express recombinant antibody molecules in the brain, which molecules are end-specific for the N-terminus or C-terminus of amyloid-β peptides, to prevent the accumulation of amyloid-β peptides in the extracellular space, interstitial fluid and cerebrospinal fluid and the aggregation of such peptides into amyloid deposits in the brain.

BRIEF DESCRIPTION OF THE DRAWINGS

FIG. 4A shows a schematic representation of the amyloid precursor protein (APP) and its functional domain; FIG. 4B is an enlargement of the Aβ peptide and its N-terminal sequences, showing the positions from which Peptides A and C were derived. FIG. 4C is the one letter amino acid code for the sequence of APP and the experimental peptides A and C.

DETAILED DESCRIPTION OF THE INVENTION

Figure 1:
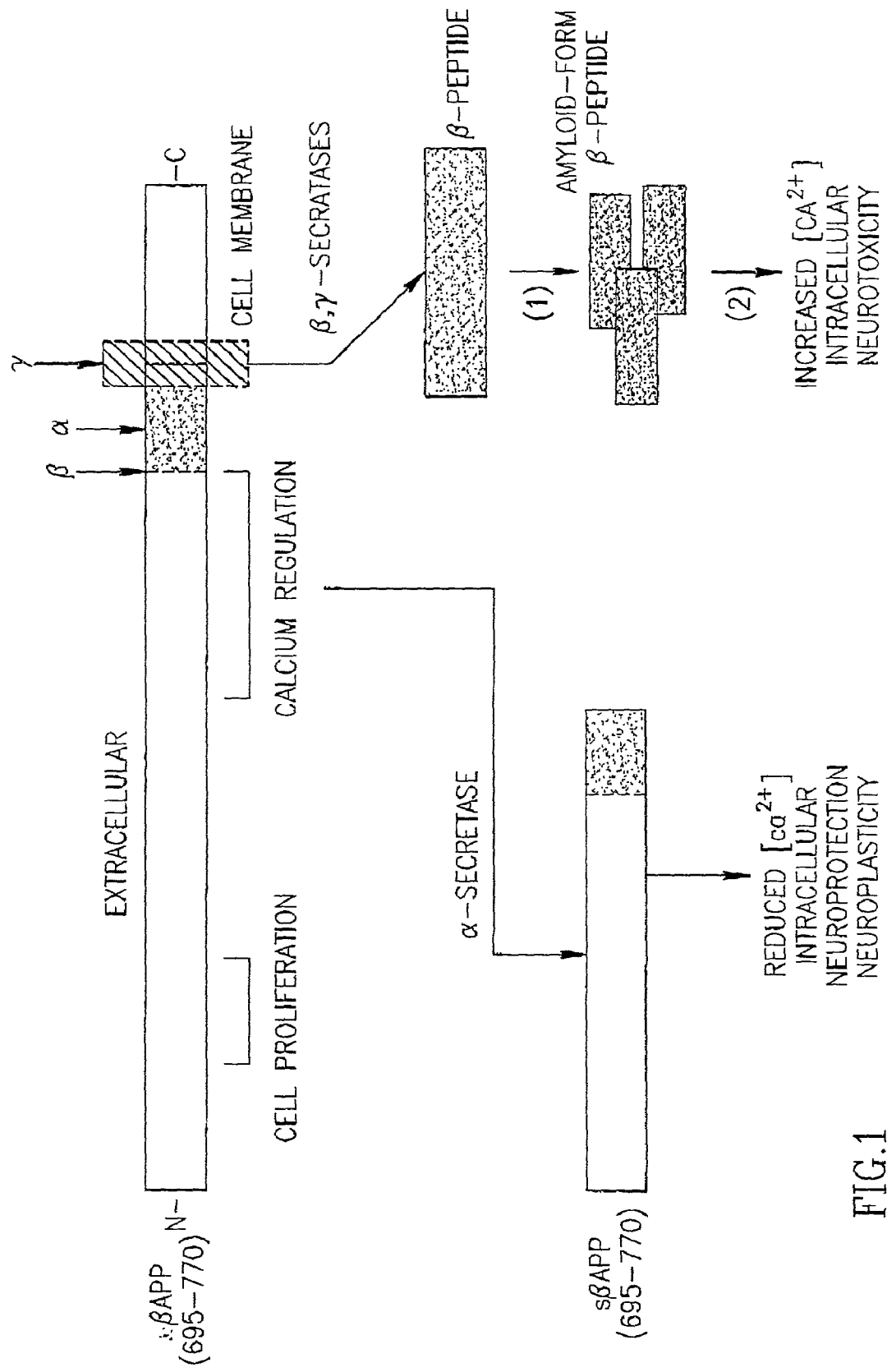
FIG. 1 shows a schematic representation of the amyloid precursor protein (APP) and the products of a, β, and γ-secretase cleavage. The general locations of various domains are indicated along with the cleavage sites (α, β, γ) for secretases
Figure 2:
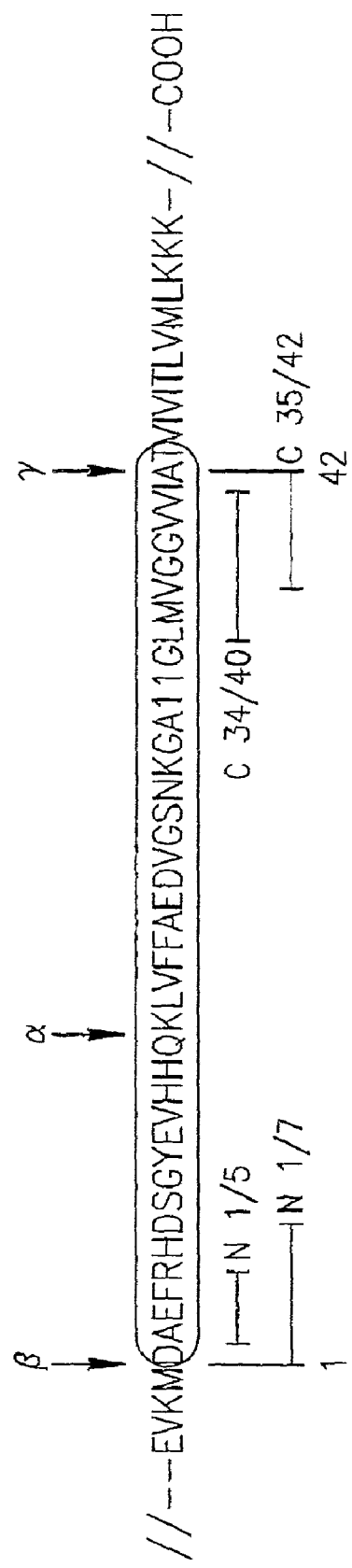
FIG. 2 shows the amino acid sequence (SEQ ID NO:1) of the region in βAPP from which β-amyloid peptides (A β) are derived. The arrows indicate the α-, β- or γ-secretase cleavage sites. The amino acid residues corresponding to the synthetic peptides that can be used as immunogens are indicated underneath the sequence by line segments.

In one embodiment, the invention relates to a method of treating a subject having Alzheimer's Disease, comprising the step of administering an antibody which is targeted to amyloid β peptide, or to fragment thereof thereby treating the subject having Alzheimer's Disease.

In another embodiment, the invention relates to a method of treating a subject having a disease or disorder, characterized by amyloid beta deposition comprising the step, of administering an antibody which is targeted to amyloid β peptide, or to fragment thereof, thereby treating the subject having a disease or disorder, characterized by amyloid beta deposition.

The other disease or disorder characterized by amyloid beta deposition are, for example without being limited, wild cognitive impairment (MCI), cerebral amyloid angiopathy or congiophylic angiopathy, Alzheimer's disease associated with Down Syndrome, and inclusion-body myositis, and.

The terms "amyloid beta", or "Aβ", or "amyloid β", or "beta amyloid" are all referred to interchangeably hereinabove to any of the amyloid β species. Such proteins are typically of about 4 kDa. Sever different amino-termini and heterogeneous carboxyl-termini sequences have been observed based on characterization of the peptide amyloid β from Alzheimer's disease tissue and from cultured cells (Glenner and Wong (1984) Biochem Biophys Res Commun 120:885-890; Joachim et al. (1988) Brain Res 474:100-111; Prelli et al. (1988) J Neurochem 51:648-651; Mori et al. (1992) J Biol Chem 267:17082-17806; Seubert et al. (1992) Nature 359:325-327; Naslund et al. (1994) Proc Natl Acad Sci USA 91:8378-8392; Roher et al. (1993) Proc Natl Acad Sci USA 90:10836-10840; Busciglio et al. (1993) Proc Natl Acad Sci USA 90:2092-2096; Haass et al. (1992) Nature 359:322-325). Specifically, with regard to the carboxyl-termini, the amyloid β peptide has been shown to end at position 39, 40, 41, 42, 43, or 44 where position 1 is the aspartate of the amyloid β sequence as defined by Glenner and Wong (1984) Biochem Biophys Res Commun 120:885-890.

While recognizing the dominant role of full-length Aβ peptides, the present invention is not limited solely to these forms. Thus, notwithstanding the importance of full-length Aβ peptides as major therapeutic targets, the invention also envisages using antibodies that are free end-specific for other Aβ peptide-derived fragments that are neurotoxic and/or can form fibrillar deposits. Importantly, free end-specific antibodies that recognize N- or C-terminus truncated Aβ-peptides species should not react with the amyloid precursor protein from which they were derived.

The terms "amyloid β fragment" or "heterogeneous amyloid β" or "truncated amyloid β" interchangeably refer to fragments derived from the full length beta amyloid peptide defined above. Biochemical studies have demonstrated that in addition to an L-aspartate at positions 1, Aβ peptides can begin with a raceminized or isomerized aspartate. Prominent N-terminus truncated Aβ isoforms begin with a cyclized glutamate (pyroglutamate) residue at position 3, pyroglutamate at position 11, and leucine at position 17 (Geddes et al 1999). Support for the fact that these isoforms contribute to the pathogenesis of Alzheimer's Disease is also based on studies which demonstrate 1) N-terminus truncated forms aggregate more readily and are more toxic in vitro than Aβ1-40 or Aβ1-42 (Pike et al. 1995) and 2) N-terminus truncated forms are among the earliest isoforms detected in plaques and may form a nidus for plaque formation (Theo et al 1995). Aβ17-42 (the p3 peptide) for example, is prevalent in AD brains but absent or sparse in aged, non-AD brains (Higgins et al. 1996). Studies of AD amyloid with high-resolution reverse-phase liquid chromatography and mass spectrometry confirm that additional N-terminus truncated forms are invariably present, including Aβn-42 (n=1–11) and Aβ3-40 (Larner 1999). Studies of Aβ secreted into media of various cultured cells and cell lines transfected with differing APP constructs have identified Aβ species beginning at positions 2, 3, 4, 5, 6, 9, 11, 16, 17, 18, 19, 20, 24 (Busciglio et al 1993, Haas et al 1992, Haas et al 1994). The "nonamyloidogenic" p3 fragment (amyloid beta 17-42) is a major coanstituent of Down's syndrome cerebellar preamyloid (Lalowski M et al., J Biol Chem Dec. 27, 1996:271(52):33623-31). Removal of this major forms, or limiting its neurotoxicity, can therefore be expected to slow progression of Down syndrome-associated Alzheimer's Disease and delay onset in susceptible individuals. Thus, the antibody of the present invention is directed in one embodiment to the N or to the C terminus of an amyloid beta peptide and in one embodiment is directed to the N or to the C-terminus of any fragment derived from the amyloid beta peptide.

By "antibody" is meant an immunoglobulin protein, which is capable of binding an antigen. Antibody as used herein is meant to include the entire antibody as well as any antibody fragments (e.g. F(ab')$_2$, Fab', Fab, Fv) capable of binding the epitope, antigen or antigenic fragment of interest. In one embodiment the antibody of the invention is a monoclonal antibody, a humanized antibody, a chimeric antibody, a bispecific antibody a scFv antibody or a F(ab) or fragments thereof.

The term "monoclonal antibody" is referred hereinabove to an immunological effective fragment as well a single chain forms.

The term "humanized antibody" is referred herein above to an antibody in which the complementary-determining regions (CDRs) of a mouse or other non-human antibody are grafted onto a human antibody framework. By human antibody framework is meant the entire human antibody excluding the CDRs.

The term "chimeric antibody" refers to an antibody in which the whole of the variable regions of a mouse or rat antibody are expressed along with human constant regions.

The term "artificial antibody" refers hereinabove to antibodies made by using molecular imprinting techniques as described in U.S. Pat. No. 5,630,978. Briefly, the method for the preparing of the artificial antibody is as follows: (i) polymerization of functional monomers around the biologically active molecule, which is the antibody to amyloid β peptide or fragment thereof (the template); (ii) removal of the template molecule; and then (iii) polymerization of a second class of monomers in the void left by the template, to provide a new organic molecule which exhibits one or more desired properties which are similar to that of the template. Thus, in one embodiment, the invention relates to artificial antibodies which are molecularly imprinted polymers (MIPs) that selectively recognize amyloid β peptides and fragments thereof and act as antibodies and to their use in treating Alzheimer's Disease and other diseases which are characterized by amyloid β deposition.

The term "treating" is referred hereinabove to delay or prevent the onset slow the progression or ameliorate the symptoms related to Alzheimer's Disease or other disease or disorder characterized by amyloid β deposition.

In another embodiment, the invention relates to a method for delaying or inhibiting or suppressing the accumulation of an amyloid β peptide or fragment thereof, comprising the step of administering an antibody which is targeted to an amyloid β peptide, or to fragment thereof, thereby delaying or inhibiting or suppressing accumulation of amyloid β peptide or fragment thereof in the brain.

In another embodiment, the invention relates to a method for delaying or inhibiting or suppressing the neurotoxicity of amyloid β peptide or fragment thereof, comprising the step of administering an antibody which is targeted to amyloid β peptide, or fragment thereof, thereby delaying or inhibiting or suppressing the neurotoxicity of amyloid β peptide or fragment thereof.

Thus, the invention relates to the use of antibodies to amyloid β peptides as a method to selectively inhibit accumulation and/or neutralize the cytotoxicity associated with amyloid β species. The most effective target for end-specific antibodies as therapy for Alzheimer's Disease is likely to be Aβ1-40, which forms the bulk of circulating amyloid β peptide human CSF, plasma, and urine), or the more toxic but less abundant Aβ1-42 and Aβ1-43 species that can seed amyloid deposition. Neuritic plaques and vascular amyloid deposits contain an abundance of these forms and the consensus that has evolved from genetic and biochemical analyses of human tissue and transgenic mouse models is that full-length forms of amyloid β peptide are the key players in the pathogenesis of Alzheimer's Disease.

The antibody or the pharmaceutical composition which contain the same, will be administered to the periphery, or a pharmaceutical composition containing an antigen to elicit such antibodies, or in another embodiment, the antibody of the invention can be added directly to the brain by intracranal or intracranially injection.

In one embodiment, the antibody of the invention will cross the blood brain barrier and will form a complex with the amyloid β protein or fragment in the brain.

In one embodiment, the invention relates to methods of treating central nervous system (CNS) conditions by peripheral administration of antibodies. The usefulness of IV Ig treatment in epilepsy was assessed by Engelen B G et al. (J. Neurol Neurosurg Psychiatry 1994 November 57 Supp 21-5). The conclusion of these authors from the study on cerebrospinal fluid IgG concentrations before and after IV Ig treatment in patients with epilepsy was that the main component of IV Ig preparation crosses the blood CSF barrier and significantly increases CSF IgG concentration, and may reach the brain and act centrally.

The presence of IgG in the central nervous system was demonstrated by immunocytochemistry and showed a close anatomical relationship between the distribution of this protein and the blood-brain barrier. IgG was immunolocalized in the normal rat brain by using monoclonal and polyclonal antibodies to IgG and its subclasses.

The passage of intravenous immunogloubulin and interactions with the CNS was summarized in a review by Wurster et al. (J. Neurol Neurosurg Psychiatry 1994 November 57 Supp 21-5).

In one embodiment, the antibody of the invention penetrates into the brain cells, through the blood brain barrier (BBB) by using methods or carriers, which details are provided below.

Preferred compounds to be added to formulations to enhance the solubility of the antibodies are cyclodextrin derivatives, preferably hydroxypropyl-gamma-cyclodextrin. Drug delivery vehicles containing a cyclodextrin derivative for delivery of peptides to the central nervous system are described in Bodor, N., et al. (1992) Science 257:1698-1700.

Accordingly, use of an antibody of the invention in combination with a cyclodextrin derivative may result in greater inhibition of β amyloid neurotoxicity than use of the modulator alone. Chemical modifications of cyclodextrins are known in the art (Hanessian, S., et al. (1995) J. Org. Chem. 60:4786-4797). In addition to use as an additive in a pharmaceutical composition containing a modulator of the invention, cyclodextin derivatives may also be useful as modifying groups and, accordingly, may also be covalently coupled to free end specific β amyloid antibody to form a modulator compound of the invention.

Low et al., U.S. Pat. No. 5,108,921, reviews available methods for transmembrane delivery of molecules such as proteins and nucleic acids by the mechanism of receptor mediated endocytotic activity. These receptor systems include those recognizing galactose, mannose, mannose-6-phosphate, transferrin, asialoglycoprotein, transcobalamin (vitamin $B_{12}$), α-2 macroglobulins, insulin and other peptide growth factors such epidermal growth factor (EGF). Low et al. also teaches that nutrient receptors, such as receptors for biotin and folate, can be advantageously used to enhance transport across the cell membrane due to the location and multiplicity of biotin and folate receptors on the membrane surfaces of most cells, and the associated receptor mediated transmembrane transport processes. Thus, a complex formed between a compound to be delivered into the cytoplasm and a ligand, such as biotin or folate, is contacted with a cell membrane bearing biotin or folate receptors to initiate the receptor mediated trans-membrane transport mechanism and thereby permit entry of the desired compound into the cell.

A biotin ligated can be attached to a DM molecule, for example, by incorporating commercially available biotinylated deoxyuucleotide triphosphates, e.g., biotin-14-MTP or biotin-14dCTP from Invitrogen Life Technologies, Carlsbad, Calif., using terminal deoxynucleotidyl transferase (Karger, B. D., 1989). Biotin-14dATP is a MTP analog with biotn attached at the 6-position of the purine base by a 14-atom linker and biotin-14-dCTP is a dCTP analog with biotin attached at the $N^4$-position of the pyrmidine base also by a 14-atom liker.

In one embodiment, the antibody of the invention can be delivered by liposomes, which is well covered in the scientific literature and in patent publications.

In another approach for enhancing transport across the BBB, a peptidic or peptidomimetic modulator is conjugated to a second peptide or protein thereby forming a chimeric protein, wherein the second peptide or protein undergoes absorptive-mediated or receptor-mediated transcytosis through the BBB. Accordingly, by coupling the modulator to this second peptide or protein, the chimeric protein is trasported across the BBB. The second peptide or protein can be a ligand for a brain capillary endothelial cell receptor ligand. For example, a preferred ligand is a monoclonal antibody that specifically binds to the transferrin receptor on brain capillary endothelial cells (see e.g., U.S. Pat. Nos. 5,182,107 and 5,154,924 and PCT Publications WO 93/10819 and WO 95/02421, all by Friden et al.), Other suitable peptides or proteins that can mediate transport across the BBB include histones (see e.g., U.S. Pat. No. 4,902,505 by Pardridge and Schimmel) and ligands such as biotin, folete, niacin, pantothenic acid, riboflavin, thiamin, pryridoxal and ascorbic acid (see e.g., U.S. Pat. Nos. 5,416,016 and 5,108,921, both by Heinstein). Additionally, the glucose transporter GLUT-1 has been reported to transport glycopeptides (L-serinyl-β-D-glucoside analogues of [Met5]enkephalin) across the BBB (Polt, R. et al. (1994) Proc. Natl Acad. Sci. USA 91:7114-1778). Accordingly, a modulator compound can be coupled to such a glycopeptide to target the modulator to the GLUT-1 glucose transporter. For example, a modulator compound which is modified at its amino terminus with the modifying group Aic (3-(O-aminoethyl-iso)-cholyl, a derivative of cholic acid having a free amino group) can be coupled to a glycopeptide through the amino group of Aic by standard methods. Chimeric proteins can be formed by recombinant DNA methods (e.g., by formation of a chimeric gene encoding a fusion protein) or by chemical crosslinking of the modulator to the second peptide or protein to form a chimeric protein. Numerous chemical crossing agents are known (e.g., commercially available from Pierce, Rockford Ill.). A crosslinking agent can be chosen which allows for high yield coupling of the modulator to the second peptide or protein and for subsequent cleavage of the linker to release bioactive modulator. For example, a biotin-avidin-based linker system may be used.

In yet another embodiment for enhancing transport across the BBB, the modulator is encapsulated in a carrier vector, which mediates transport across the BBB. For example, the modulator can be encapsulated in a liposome, such as a positively charged unilamellar liposome (see e.g., PCT Publications WO 88/07851 and WO 88/07852, both by Faden) or in polymeric microspheres (see e.g., U.S. Pat. No. 5,413,797 by Khan et al., U.S. Pat. No. 5,271,961 by Mathiowitz et al. and 5,019,400 by Gombotz et al.). Moreover, the carrier vector can be modified to target it for transport across the BBB. For example, the carrier vector (e.g., liposome) can be covalently modified with a molecule which is actively transported across the BBB or with a ligand for brain endothelial cell receptors, such as a monoclonal antibody that specifically binds to transferrin receptors (see e.g., PCT Publications WO 91/04014 by Collins et al. and WO 94/02178 by Greig et al.)

A method for preventing or inhibiting the progression of Alzheimer's Disease in accordance with the present invention, involves delivering a gene encoding the antisenilin molecule into brain cells where antisenilins are then stably expressed and secreted into the extracellular space, interstitial fluid and cerebrospinal fluid. The secretion of antisenilins into the extracellular space, interstitial fluid and cerebrospinal fluid, where soluble Aβ peptides are present, promotes the formation of soluble antisenilin-Aβ complexes.

A antibody of the invention can be formulated into a pharmaceutical composition wherein the antibody is the only active compound or, alternatively, the pharmaceutical composition can contain additional active compounds. For example, two or more antibody compounds may be used in combintion. Moreover, an antibody of the invention can be combined with one or more other agents that have anti-amyloidogenic properties. For example, an antibody can be combined with the non-specific cholinesterase inhibitor tacrine (COGNEX.RTM., Parke-Davis).

Other methods that may be developed from time to time are also contemplated.

Once delivered into the brain the specific antibody molecules will transfer into the extracellular space, interstitial fluid and cerebrospinal fluid. The specific antibody molecules then form a soluble complex with Aβ peptide. These soluble specific-Aβ peptide-antibody complexes reduce, in one embodiment, the deposition of Aβ peptides into amyloid plaques and attenuate Aβ peptide-induced neurotoxicity by clearing Aβ peptides from the central nervous system through drainage of the extracellular space, interstitial fluid and cerebrospinal fluid into the general blood circulation where they will be eliminated by protease digestion. Accordingly, the accumulation of newly secreted soluble Aβ peptides responsible for amyloid deposition and Aβ-induced neurotoxicity is inhibited.

Furthermore, clearance of soluble amyloid-β peptides in accordance with the present invention is expected to reduce the inflammatory process observed in Alzheimer's Disease by inhibiting, for example, amyloid -β-induced complement activation and cytokine release, and blocking also the interaction of Aβ with cell surface receptors such as the RAGE receptor.

In another embodiment, once the antibodies of the invention bind to the amyloid β peptide they can elicit a cellular immune response (i.e. via activation of the Fc receptor). Fc receptor can distinguish between an antibody, which is bound to an antigen, and a free antibody. The result will be that the Fc receptors will enable accessory cells, which are usually not capable of identifying target antigens to target and engulf amyloid β peptide. In this scenario, the requirement for a stoichiometric relationship between antibody and antigen may be eliminated. As a consequence, less free-end specific antibody will be required to penetrate the BBB for elimination of deposited amyloid β peptides.

In another embodiment, the interaction of Aβ with APOE4 gene product will be reduced by the adding of the antibody of the invention.

In one embodiment, the antibody or the pharmaceutical composition which contain the same, will block peripheral Aβ peptide from entering the CNS, thus reducing accumulation of amyloid plaques in the brain.

In another embodiment, the pharmaceutical composition and the antibodies of the present invention will delay the onset and inhibit or suppress the progression of Alzheimer's Disease by having a peripheral effect. The clearance or the removal of the amyloid beta from the periphery will change the equilibrium of the amyloid beta in the blood and as a result in the brain. Recent studies have shown that amyloid beta is transported from the cerebrospinal fluid to the plasma with an elimination half-life from brain of about half an hour. Thus, the antibody can affect the amyloid beta level in the plasma, cause accumulation of central amyloid beta in the plasma and as a result reduce the amyloid β deposition in the brain.

In one embodiment, the invention provides an antibody molecule which is free end-specific for the N-terminus or the C-terminus of an amyloid β peptide and/or fragments thereof which is capable of discrimination between an Aβ peptide and the amyloid protein precursor. The term "free end specific " means a molecule which binds specifically to a free terminus/end of an Aβ peptide or to any fragment thereof to slow down or prevent the accumulation of amyloid-β peptides in the extracellular space, interstitial fluid and cerebrospinal fluid and to block the interaction of Aβ peptides with other molecules that contribute to the neurotoxocity of Aβ.

Figure 4:
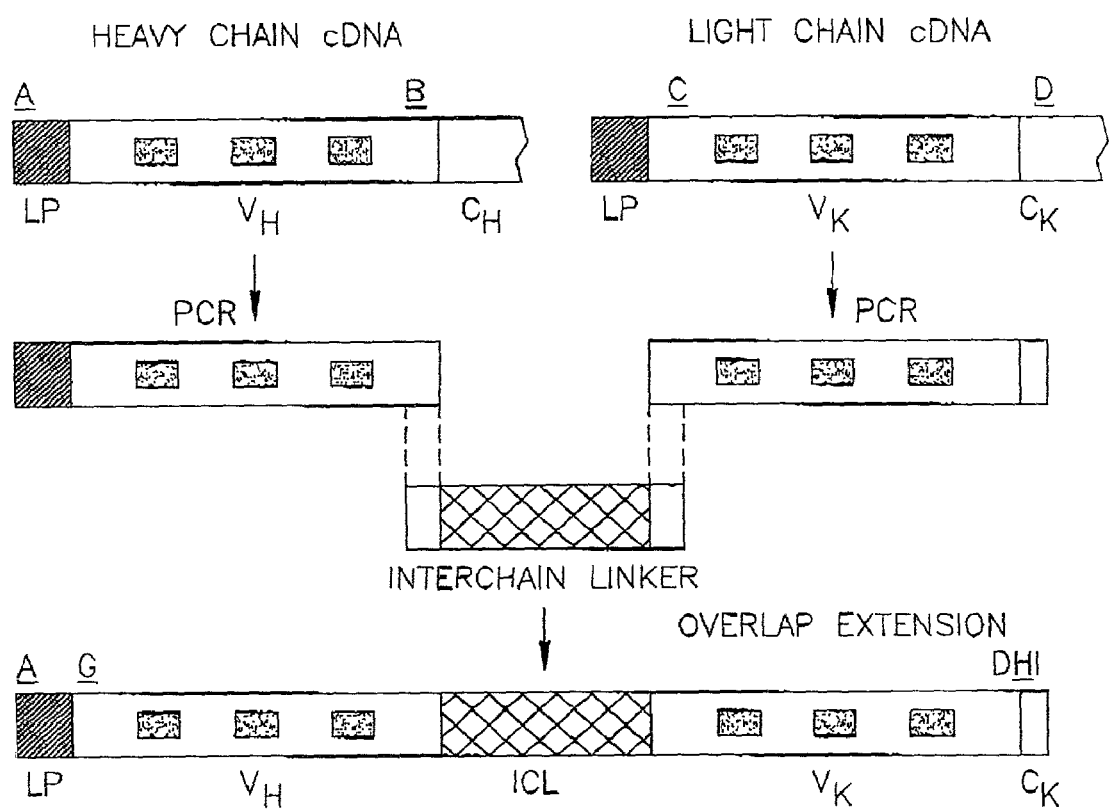
FIG. 4 A-C.
Figure 5:
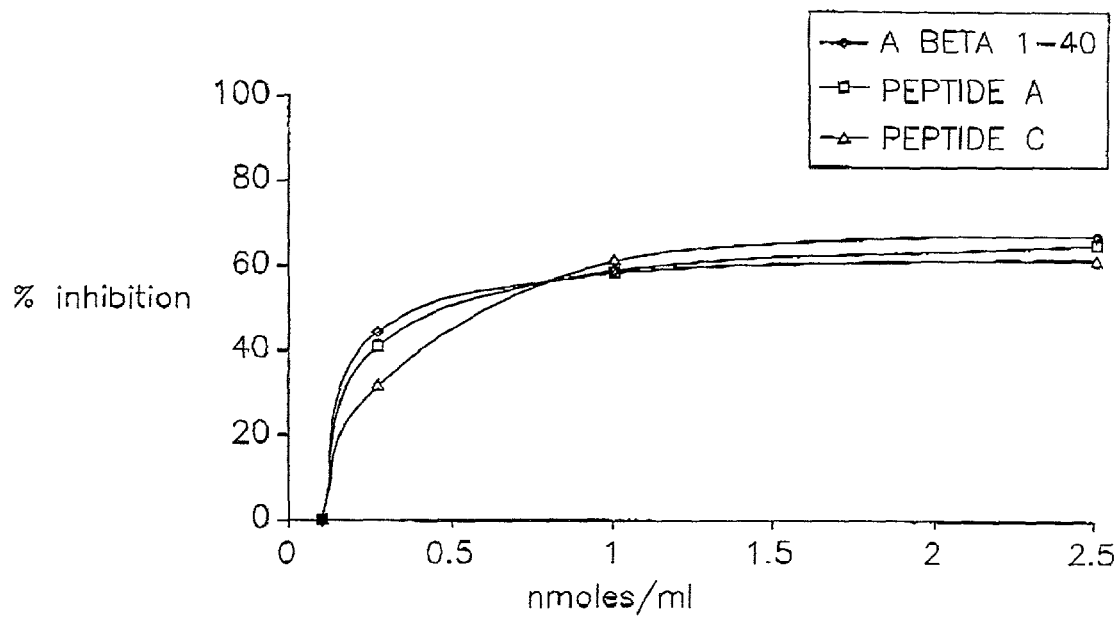
FIG. 5 shows the generation of epitope-specific antibodies. Specific binding of Sample 1 to the immungen (Peptide A) in a standard ELISA assay is inhibited by the same peptide, by the $Aβ_{1-40}$ Peptide and by Peptide C, which spans the cleavage site of Aβ within the precursor molecule APP.
Figure 6:
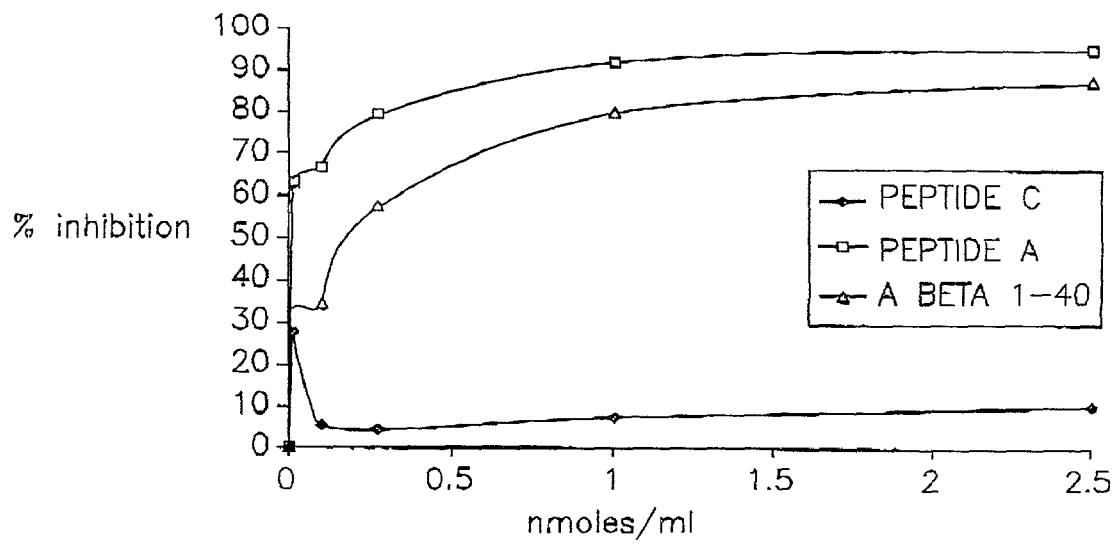
FIG. 6 shows the generation of free end-epitope-specific antibodies. Specific binding of Sample 2 to the inmungen (Peptide A) in a standard ELISA assay is inhibited by the same peptide, by the $Aβ_{1-40}$ Peptide but NOT by Peptide C, which spans the cleavage site of Aβ within the precursor molecule APP.

Without being limited, the method of detecting provides an antibody molecule which is free end-specific for the N-terminus or the C-terminus of an amyloid β peptide and/or fragments thereof namely, the 'spanning peptide ELISA detection method' is as follows: antibodies that bind sequences in the N-terminus region of amyloid β peptide, (for example residues 1-5 of Peptide A or Asp-Ala-Glu-Phe-Arg (SEQ ID NO: 14); see FIG. 4), and also bind the identical sequence of amino acids in the spanning peptide C, which corresponds to sequences of the amyloid precursor protein (APP), are eliminated from the screen. Only antibodies that bind ($NH_2$)Asp-Ala-Glu-Phe-Arg (SEQ ID NO: 14) with a free N-terminus (for example, the heptamer peptide or full length Aβ1-40), but do not bind the spanning peptide, are selected in this detection system. These selected antibodies should be described as 'free N-end-specific' because their binding epitope incorporates both a high affinity recognition element for a free amino (NH$_2$) group, in addition to recognition of the N-terminal amino acid residues of the particular amyloid-β peptide. A similar detection system is envisaged for selecting antibodies that are C-end-specific using a spanning peptide that corresponds to a contiguous sequence of amino acids on both sides of the C-terminal cleavage sites in APP. This exquisite sensitivity of free-end specific antibodies is required so as not to affect the normal biological functions of the transmembrane receptor-like APP molecule that is implicated in several important physiological roles (such as mediation in adhesion, growth promoting effects, neuroprotection, neuritic outgrowth, recycling of synaptic vesicles, regulation of apoptosis inhibition of serine proteases, receptor and signal transduction functions, calcium metabolism and nucleic acid transcription). Thus, in one embodiment, the invention utilizes free-end specific antibodies to inhibit the accumulation of amyloid β peptides, to ameliorate or prevent the neurotoxic consequences of amyloid deposition, to slow Alzheimer's Disease or other diseases characterized by amyloid β deposition progression or to delay their onset.

In another embodiment, the invention relates to an antibody that is free-end specific and is targeted to the free N-terminus of amyloid β-peptide. In another embodiment the invention relates to an antibody that is free-end specific and is targeted to the free N-terminus of amyloid β-peptide, wherein the first amino acid of the free N-terminus of amyloid β-peptide is aspartate.

In another embodiment, the invention relates to an antibody that is free-end specific and is targeted to the free N terminus of N- and/or C-terminus-truncated amyloid β peptide fragment.

In one embodiment, the free end specific antibody is specific to amino acids 1-3 of the N-terminus-truncated amyloid β-peptide in addition to a free amino (NH$_2$) group. In one embodiment, the free end specific antibody is specific to amino acids 1-4 of the terminus-truncated amyloid β-peptide in addition to a free amino (NH$_2$) group. In one embodiment, the free end specific antibody is specific to amino acids 1-5 of the N-terminus-truncated amyloid β-peptide in addition to a free amino (NH$_2$) group. In one embodiment, the free end specific antibody is specific to amino acids 1-6 of the N-terminus-truncated amyloid β-peptide in addition to a free amino (NH$_2$) group. In one embodiment, the free end specific antibody is specific to amino acids 1-7 of the N-terminus-truncated amyloid β-peptide in addition to a free amino (NH$_2$) group. In one embodiment, the free end specific antibody is specific to amino acids 1-8 of the N-terminus-truncated amyloid β-peptide in addition to a free amino (NH$_2$) group.

As shown in Examples the 'spanning peptide ELISA detection method' may also be applied to the free N-terminus of any one of the N-terminus-truncated amyloid β-peptides species that are found to be important in the pathogenesis of Alzheimer's disease (Masters C L et al 1985, Haass et al 1993, Miller D L et al 1993, Vigo-Pelfrey C et al. 1993, Naslund et al 1994, Theo T C et al 1995). The present specification describes in one embodiment the use of short peptides such as SEQ ID NO:2 (Asp-Ala-Glu-Phe-Arg-Cys) and SEQ ID NO:3 (Asp-Ala-Glu-Phe-Arg-His-Asp-Cys that correspond to the amino acid sequence at the N-terminus of amyloid β peptide starting at position 1 (Asp) as examples of immunogens for the production of free end-specific antibodies. When using these inmunogens, in one embodiment the lack of reactivity with a spanning peptide (SEQ ID NO.7 Glu-Ile-Ser-Glu-Val-Lys-Met-Asp-Ala-Glu-Phe-Arg-His) in the 'spanning peptide ELISA detection method' is tested.

Similarly, immunization or selection with sequences corresponding to N-terminus-truncated amyloid β-peptides species such as Aβ11-40/42, followed by screening with the appropriate spanning peptide could also be employed in this invention. Examples of such sequences are included herein: SEQ ID NO:9 Glu-Val-His-His-Gln-Cys, corresponding to residues 11-15 of the full length Aβ peptide, with an additional cysteine residue for conjugation purposes is an example of an immunizing peptide; SEQ SED NO:10 Phe-Arg-His-Asp-Ser-Gly-Tyr-Glu-Val-His-His-Gln is an example of a spanning peptide which would be used in the 'spanning peptide ELISA detection method' in order to isolate end-specific antibodies.

In another embodiment, the invention relates to an antibody that is free-end specific and is targeted to the free C-terminus of the amyloid β-peptide Aβ1-39, Aβ1-40, Aβ1-41, or Aβ1-43.

On another embodiment, the invention relates to a single chain antibody that is free-end specific and is targeted to the free C-terminus of the amyloid β-peptide Aβ1-42.

In another embodiment there is provided an antibody which is free-end specific for the free C-terminus of the amyloid β-peptide Aβ1-40, which antibody does not bind to the amyloid β-precursor protein from which the amyloid β peptide is proteolytically derived.

In another embodiment there is provided an antibody free-end specific for the free C-terminus of the amyloid β-peptide Aβ1-43 which antibody does not bind to the amyloid precursor protein from which the amyloid β-peptide is proteolytically derived.

In another embodiment, the invention relates to an antibody that is free-end specific and is targeted to the free C-terminus of N- and/or C-terminus-truncated amyloid β peptide fragment. Thus, the invention also addresses heterogeneity at the C-terminus where the longer forms, namely, Aβ42/3, are more prone to aggregate as fibrils and can lead to aggregation of the more abundant Aβ1-40. For example without being limited, the invention envisages the therapeutic use of antibodies that are free end-specific for the C-terminus of each of the forms Aβx-39, Aβx40, Aβx-41, Aβx-42 and Aβx43. For example, in one embodiment, Aβ 42 has the following sequence:

H$_2$N-Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala-OH (SEQ ID NO: 15).

Aβ41, Aβ40 and Aβ39 differ from Aβ42 by the omission of Ala, Ala-Ile and Ala-Ile-Val respectively from the C-terminal end. Aβ43 differs from Aβ42 by the presence of a threonine at the C-terminus.

As examples, in one embodiment the use of certain antigenic sequences corresponding to short regions at the C-terminus of amyloid β peptide are described by SEQ ID No:4 Cys-Leu-Met-Val-Gly-Gly-Val-Val (Aβx-40), and SEQ ID No: 11 Cys-Gly-Gly-Val-Val-Ile-Ala-Thr (Aβx-43). Spanning peptides which may be used to detect C-terminal end-specific antibodies in the 'spanning peptide ELISA detection method' are SEQ ID NO: 12 (Asn-Lys-Gly-Ala-Ile-Ile-Gly-Leu-Met-Val-Gly-Gly-Val-Val) and SEQ ID NO: 13 (Ala-Ile-Ile-Gly-Leu-Met-Val-Gly-Gly-Val-Val-Ile-Ala-Thr), for Aβx-40 and Aβx43, respectively. Analogous peptides can be designed for targeting Aβx42 species. Thus, for example, without being limited, in a representative example using amyloid β1-40, in one embodiment, the free end specific antibody is targeted to amino acids 33-40 of the C-terminus-truncated amyloid β-peptide in addition to a free carboxylic (COOH) group. In one embodiment, the free end specific antibody is targeted to amino acids 34-40 of the C-terminus-truncated amyloid β-peptide in addition to a free carboxylic (COOH) group. In one embodiment, the free end specific antibody corresponds to amino acids 36-40 of the C-terminus-truncated amyloid β-peptide in addition to a free carboxylic (COOH) group. In one embodiment, the free end specific antibody corresponds to amino acids 37-40 of the C-terminus-truncated amyloid β-peptide in addition to with a free carboxylic (COOH) group. Please note that the amyloid β-peptide 1-40 served as a representative example; the same fragments can be derived from amyloid β-peptide 1-39, 1-41, 1-42 and 1-43.

As shown in FIG. 1 (see Schehr, 1994), and discussed in the Background Art section, the amyloid protein precursor (APP) is believed also to serve as a precursor for a proteolytic product, soluble -amyloid protein precursor (sAPP), thought to have growth promoting and neuroprotective functions. It will be readily appreciated by those of skill in the art that the introduction/administration of free end specific molecules will not interfere with the normal biological functions of APP or sAPP that are not associated with the formation of Aβ peptides.

Figure 3A:
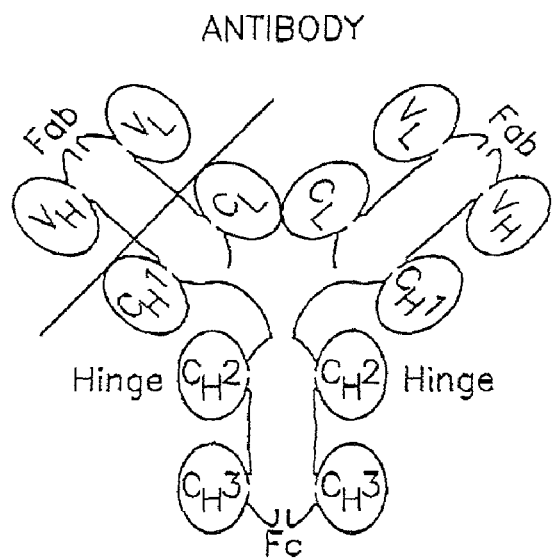
FIGS. 3A-3D schematically show the structure of a whole antibody (FIG. 3A, with the variable domain of heavy ($V_H$) and light ($V_L$) chains and the constant domain(s) of light ($C_L$) and heavy ($C_H1$, $C_H2$, $C_H3$) chains, a Fab fragment (FIG. 3B), a Fv fragment (FIG. 3C), and a single chain Fv fragment (scFv) (FIG. 3D). The Fab fragment shown in FIG. 3B consists of a variable domain of heavy $V_H$ and light $V_L$ chain and the first constant domain ($C_H1$ and $C_L$) joined by a disulfide bridge. The Fv fragment shown in FIG. 3C represents the antigen binding portion of an antibody formed by a non-covalently linked variable region complex ($V_H$-$V_L$), whereas the single chain Fv shown in FIG. 3D joins the variable heavy $V_H$, with the variable light $V_L$, chain via a peptide linker.
Figure 3B:
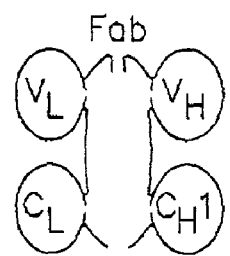
Figure 3C:
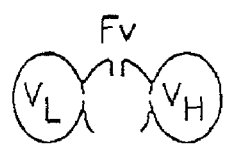
Figure 3D:
Figure 3D:

Single-chain antibodies as free end specific molecules can also be produced according to the present invention. These single chain antibodies can be single chain composite polypeptides having free end -specific Aβ peptide binding capability and comprising a pair of amino acid sequences homologous or analogous to the variable regions of an immunoglobulin light and heavy chain (linked $V_H$-$V_L$, or single chain Fv). Both $V_H$ and $V_L$ may copy natural antibody sequences, or one or both of the chains may comprise a CDR construct of the type described in U.S. Pat. 5,091,513. The separate polypeptides analogous to the variable regions of the light and heavy chains are held together by a peptide linker. Methods of production of such single chain antibodies, e.g., single Fv (scFv), particularly where the DNA encoding the polypeptide structures of the $V_H$ and $V_L$ chains are characterized or can be readily ascertained by sequence analysis, may be accomplished in accordance with the methods described, for example, in U.S. Pat. No. 4,946,778, U.S. Pat. No. 5,091,513, U.S. Pat. No. 5,096,815, Biocca et al., 1993, Duan et al., 1994, Mhashilkar et al., 1995, Marasco et al., 1993, and Richardson et al., 1995. FIGS. 3A-3D (from Biocca et al., 1995) schematically show an intact antibody (FIG. 3A), a Fab fragment (FIG. 3B), a Fv fragment consisting of a non-covalently linked variable region complex (V, -V, (FIG. 3C) and a single chain Fv antibody (FIG. 3D).

The design of immunogenic peptides for use in immunization in an animal and the generation of antibody producing hybridomas is based on similar peptides that have been previously used by several laboratories to generate polyclonal antibodies for in vitro use, that recognize the free termini of Aβ species (Harrington et al., 1993; Iwatsubo et al., 1994; Konig et al., 1996; Murphy et al., 1994; Gravina et al., 1995). While peptides of longer lengths have in some instances been used successfully to generate Aβ end-specific antibodies, Theo and co-workers (1993; 1994) established that there is a length of five amino acids for any given peptide which ensures that the specific free to group at the N-terminus constitutes an essential part of the epitope recognized by the new antibody. Thus, an antibody generated against an immunogenic peptide is evaluated for the selectivity of the antibody in its recognition of a free N- or C-terminus of an Aβ peptide. A competitive inhibition assay, using Enzyme-Linked Immunosorbaat Assay (ELISA) or immunoprecipitation with peptides corresponding to different regions of Aβ and the region immediately preceding the β-secretase cleavage site in the extracellular domain of βAPP, can determine the selectivity of the antibody.

Those of skill in the art will appreciate that a cysteine residue can be added to the end of the above immunogenic peptides opposite from the end corresponding to the free N-terminus or the free C-terminus of Aβ peptides to facilitate coupling to a carrier protein. Keyhole limpet hemocyanin (KLH), ovalbumin and bovine serum albumin (BSA) are non-limiting examples of proteins that can be used as carriers for immunogens. The presence of an N-terminal or C-terminal cysteine residue on the synthetic immunogen peptides provides a free sulfhydryl group for covalent coupling to a maleimide-activated protein. A heterobifunctional reagent, such as an N-madeimido-6-aminocaproyl ester or a m-maleimidobeczoyl-N-hydroxysuccinimide ester (MBS), is used to covalently couple the synthetic immunogenic peptide to the carrier protein (see for example, Hartlow, E. et al., Antibodies A Laboratory Manual, Cold Spring Harbor Laboratory Press, Cold Spring Harbor, N.Y. 1988). Commercial kits are also readily available for use in coupling peptide antigens to maleimide-activated large carrier proteins.

The invention further provides a hybridoma cell producing monoclonal antibody or a single chain antibody that is free end-specific for the N-terminus or the C-terminus of an amyloid β peptide or fragment thereof and discriminates between an Aβ peptide and the amyloid protein precursor from which it is proteolytically derived. The hybridomas producing the monoclonal antibodies of the present invention are produced following the general procedures described by Kohler and Milstein, Nature, 256, p. 495 (1975). In that procedure, hybridomas are prepared by fusing antibody-producing cells (typically spleen cells of mice previously immunized with an amyloid beta as antigen source) to cells from an immortal tumor cell line using somatic cell hybridization procedures.

For the production of antibodies, various hosts including goats, rabbits, rats, mice, humanized mice, humans, and others may be immunized by injection with the relevant epitope or with any fragment or oligopeptide thereof, which has immunogenic properties. Depending on the host species, various adjuvants may be used to increase immunological response. Such adjuvants include, but are not limited to, Freund's, mineral gels such as aluminum hydroxide, and surface-active substances such as lysolecithin, pluronic polyols, polyanions, peptides, oil emulsions, KLH, and dinitrophenol.

The hybridomas resulting from the fusion process are allowed to grow. Thereafter, the resulting supernatants are screened using immunoassay procedures to detect antibodies present in the supernatants capable of binding to the specific antigens.

In another embodiment combinatorial antibody library technology, i.e., antigen based selection from antibody libraries expressed on the surface of M13 filamentous phage, can be used for the generation of monoclonal antibodies and possesses a number of advantages relative to hybridoma methodologies (Huse, et al, 1989. Barbas, et al. 1991; Clackson, et at, 1991: Burton and Barbas, 1994). The antibody of the invention may be generated from phage antibody libraries. The general methodologies involved in creating large combinatorial libraries using phage display technology is described and disclosed in U.S. Pat. No. 5,223,409 issued Jun. 29, 1993.

Once monoclonal antibodies are generated, the selectivity and binding affinity (Kd) can be evaluated by ELISA, and in vitro bioassays can be performed on the antibodies to test for the efficacy of the Aβ end -specific antibodies in blocking Aβ-induced cytotoxicity. In vitro bioassays can also be performed on the antibodies to test for the lack of interference with function of the amyloid precursor protein APP.

In another embodiment, the antibodies will be produced in vivo, in the subject in need, by administering of an antigen such as amyloid β peptide or fragments thereof. The titer of the antibodies will be determined by techniques which are known to one skilled in the art and additional antigen will be administered if required.

In another embodiment there is provided a pharmaceutical composition comprised of the antibodies described above and a method of using the composition for the inhibition of the accumulation of amyloid β peptides in the extracellular milieu of a neuron. The diminished accumulation of amyloid β peptides will fewer delay the progression of the Alzheimer's Disease or other diseases characterizd by amyloid beta deposition, in a subject in need.

In one embodiment, the composition includes an antibody in a therapeutically or prophylactically effective amount sufficient to inhibit the neurotoxicity of natural β amyloid peptides, and a pharmaceutically acceptable carrier. A "therapeutically effective amount" refers to an amount effective, at dosages and for periods of time necessary, to achieve the desired therapeutic rest, such as slowed progression of Alzheimer's Disease, delayed onset, reduction or reversal of amyloid β deposition and/or reduction or reversal of Aβ neurotoxicity. A therapeutically effective amount of the antibody of the invention may vary according to factors such as the disease state, age, sex, and weight of the individual, and the ability of the modulator to elicit a desired response in the individual. Dosage regimens may be adjusted to provide the optimum therapeutic response. A therapeutically effective amount is also one in which any toxic or detrimental effects of the modulator are outweighed by the therapeutically beneficial effects.

A "prophylactically effective amount" refers to an amount effective, at dosages and for periods of time necessary, to achieve the desired prophylactic result, such as preventing or inhibiting the rate of amyloid deposition and/or amyloid β neuxotoxicity in a subject predisposed to amyloid β deposition. A prophylactically effective amount can be determined as described above for the therapeutically effective amount. Typically, since a prophylactic dose is used in subjects prior to or at an earlier stage of disease, the prophylactically effective amount will be less than the therapeutically effective amount.

One factor that may be considered when determining a therapeutically or prophylactically effective amount of an antibody to amyloid β is the concentration of natural amyloid β in a biological compartment of a subject, such as in the cerebrospinal fluid (CSF) or the plasma of the subject. It is to be noted that dosage values may vary with the severity of the condition to be alleviated. It is to be further understood that for any particular subject, specific dosage regimens could be adjusted over time according to the individual need and the professional judgment of the person administering or supervising the administration of the compositions. For example, a single bolus may be administered, several divided doses may be administered over time or the dose may be proportionally reduced or increased as indicated by the exigencies of the therapeutic situation.

The pharmaceutical composition can be administered subcutaneously, intravenously, intradermally, intramuscularly, intraperitoneally, intracerebrally, intranasally, orally, transdermally, buccally, intra-arterially, intracranially, or intracephalically. It is especially advantageous to formulate parenteral compositions in dosage unit form for ease administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals. As used herein "pharmaceutically acceptable carrier" includes any and all solvents, dispersion media, coatings, antibacterial and antifungal agents, isotonic and absorption delaying agents, and the like that are physiologically compatible. In one embodiment, the carrier is suitable for parenteral administration. Preferably, the carrier can be suitable for intravenous, intraperitoneal or intramuscular administration. Alternatively, the carrier is suitable for administration into the central nervous system (e.g., intraspinally or intracerebrally). In another embodiment, the carrier is suitable for oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the antibody can be administered in a time-release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Figure 7:
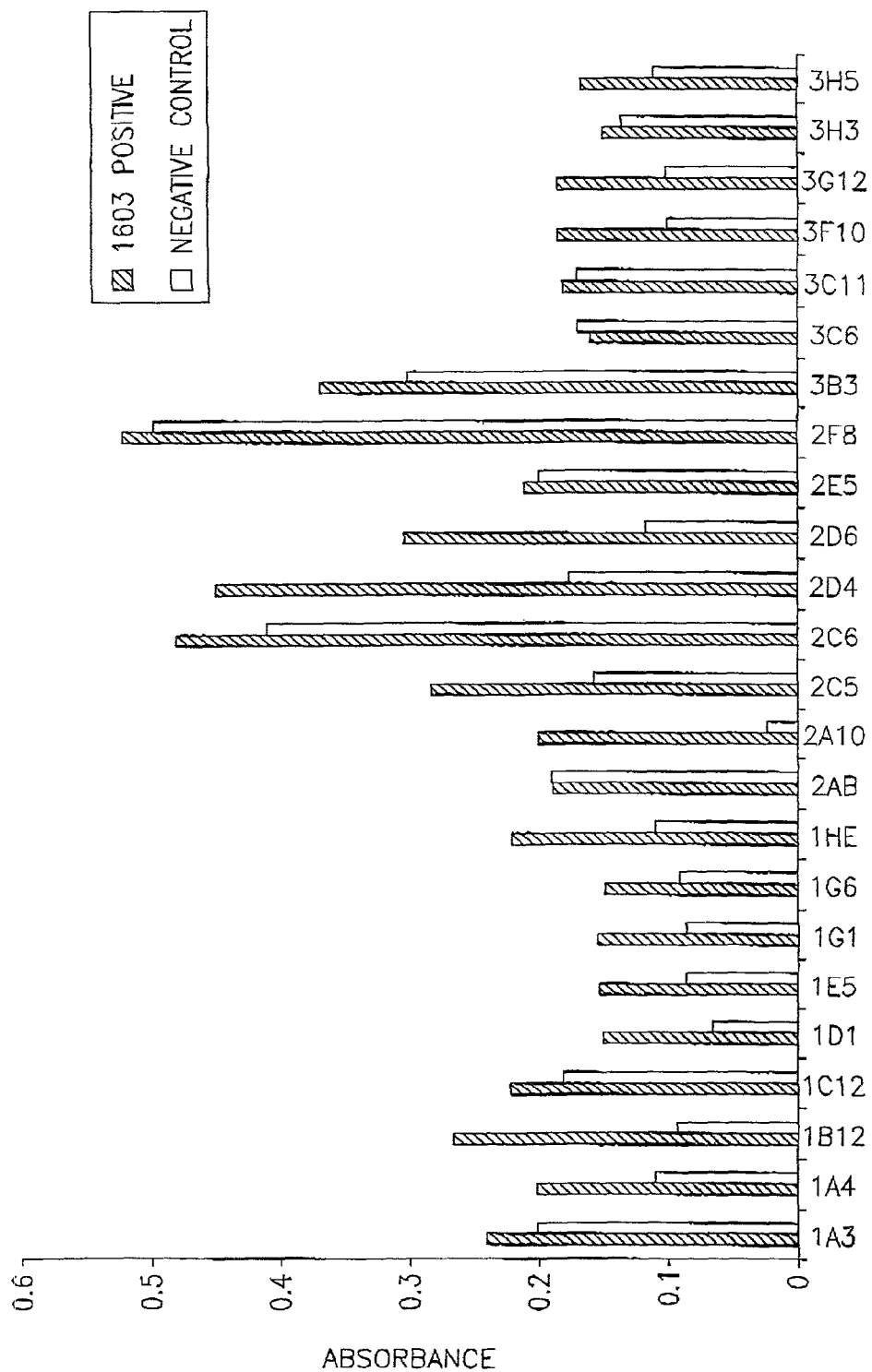
FIGS. 7 and 8 show the generation of free end-epitope-specific hybridomas. Clones 4D12 and 2A10 are two examples of hybridomas, which recognize the positive control immunizing peptide much greater than they recognize the negative control spanning peptide.
Figure 8:
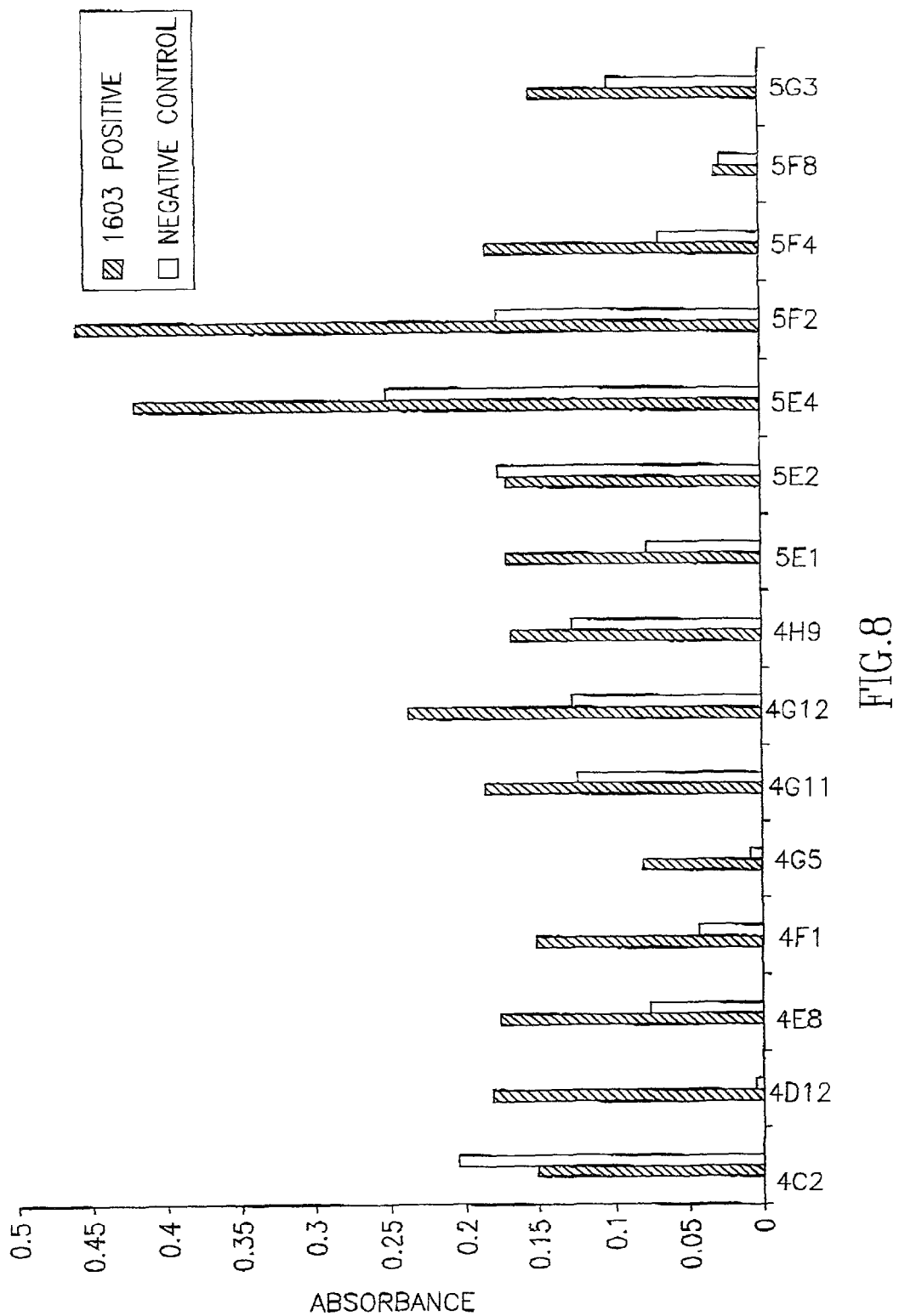

Sterile injectable solutions can be prepared by incorporating the active compound (e.g., antibody to amyloid β in the required amount) in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation awe vacuum drying and freeze-drying which yields a powder of the active ingredient plus any additional desired ingredient from a previously sterile-filtered solution thereof.

Topical application can result from intransdermal or intradermal application. Topical administration can be facilitated by coadministration of the agent with cholera toxin or detoxified derivatives or subunits thereof. Alternatively, transdermal delivery can be achieved using skin patch or using transferosomes.

Other delivery systems can include time-release, delayed release or sustained release delivery systems. Such systems can avoid repeated administrations of the active compounds of the invention, increasing convenience to the subject and the physician. Many types of release delivery systems are available and known to those of ordinary skill in the art. They include polymer based systems such as polylactic and polyglycolic acids polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. In addition, a pump-based hardware delivery system can be used, some of which are adapted for implantation.

A long-term sustained release implant also may be used "Long-term" release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above. Such implants can be particularly useful in treating conditions characterized by aggregates of amyloid β peptides by placing the implant near portions of the brain affected by such aggregates, thereby effecting localized, high doses of the compounds of the invention.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

EXAMPLES

Having now generally described the invention, the same will be more readily understood through reference to the following examples, which are provided by way of illustration ad are not intended to be limiting of the present invention.

Example 1

Demonstration of the 'spanning peptide' ELISA detection methodology in detecting antibodies that are free-end specific for amyloid β peptides Peptide $H_2N$-Asp-Ala-Glu-Phe-Arg-aminohexanoate-Cys-amide (SEQ ID NO: 16) was conjugated to BSA through a SMCC linker. Swiss Webster mice were immunized with 100 μg of this conjugate in Freund's complete adjuvant and then boosted twice with a further 100 μg of conjugate in Freund's incomplete adjuvant. Antisera were screened using the 'spanning peptide ELISA detection method', as described in the specification. Briefly, Aβ1-40 was coated onto 96-well plates, which were then incubated with samples in the presence of competing peptides A (immunogen), C (spanning peptide), or Aβ1-40 itself. The common result is shown in FIG. 5. As expected, antibodies produced by these animals bind residues 1-5 of AP (peptide A), which was the peptide used for immunization, and the full-length Aβ1-40 peptide. However, these antibodies are also reactive with the Aβ1-5 epitope when flanked by additional sequences on its N-terminus (peptide C), as is the case in the intact amyloid precursor protein APP. Such antibodies may be referred to as epitope-specific (for sequences 1-5 of the N-terminus of Aβ).

A much more rare result seen upon testing of samples is shown in FIG. 6. These antibodies bind the immunizing peptide (Aβ1-5) and the Aβ1-40 sequence, but do not recognize the peptide derived from the region which spans the same 5 amino acid sequence in the full length APP (peptide C). The exquisite selectivity of these antibodies lies in their ability to bind the 1-5 sequence only when positioned at the free N-terminus of the molecule; these antibodies are referred to as free end-specific.

Example 2

Demonstration of the "spanning peptide" ELISA detection methodology in selecting hybridomas that are free-end specific for amyloid β peptides Peptide $H_2N$-Asp-Ala-Glu-Phe-Arg-His-aminohexanoate-Cys-amide (SEQ ID NO: 16) was conjugated to KLH through an MBS linker Balb/c x C57B1/6 F1 mice were am immunized with 50 μg of this conjugate in Freund's complete adjuvant and then boosted four times with a further 50 μg of conjugate in Freund's incomplete adjuvant. Antisera were tested and fusions performed using standard methods. Hybridomas were screened using the 'spanning peptide ELISA detection method', as described in the specification. Briefly, either positive peptide (H₂N-Asp-Ala-Glu-Phe-Arg-His (SEQ ID NO: 6) conjugated to BSA) or negative control 'spanning' peptide (acetyl-Glu-Val-Lys-Met-Asp-Ala-Glu-Phe-Arg-His) (SEQ ID NO: 17) were coated onto 96-well plates, which were then incubated with hybridoma supernatants. As seen in FIGS. 7 and 8, some hybridomas recognize both peptides in a similar manner (i.e. clones 5E2, 2A8, and 2F8) or with insignificant differences (i.e. clones 4H9, 1C12, and 3H3). However, some clones demonstrate free-end specificity in that they recognize the positive peptide used for immunization much greater than they recognize the negative control spanning peptide, which in fact contains the same sequence used for immunization. Examples are seen in clones 4D12 and 2A10 of this fusion.

Example 3

Prophetic Experiments

In vitro bioassays to test efficacy of Aβ end-specific antibodies in blocking Aβ fibril formation and Aβ-induced cytotoxicity Aβ-induced neurotoxicity The receptor for advanced glycation end products (RAGE) mediates some of the neurotoxic effects of Aβ on neurons and microglia (Yan et al., 1996).

End-specific antibodies are tested for their ability to inhibit the receptor-mediated neurotoxicity by competitive inhibition. The antibodies are tested both with purified RAGE receptor preparations and by measuring their effect on Aβ-induced cellular oxidant stress.

The RAGE receptor is purified from a bovine lung extract dissolved in tris-buffered saline containing octyl-p-glucoside (1%) and phenylmethylsulfonylfluoride (2 nm) and applied to a heparin hyperD column (Biosepra). The column is eluted with a gradient of NaCl and fractions with maximal binding of $^{125}$I-labeled Aβ are identified. The fractions are pooled and loaded onto hydroxyapatite ultragel (Biosepra) and eluted with increasing concentrations of phosphate.

Fractions with maximal binding of $^{125}$I-labeled. Aβ are applied to preparative non-reduced polyacrylide SDS gels (10%).

The RAGE receptor protein $M_r$ 50,000 is identified by Coommassie Blue staining and the region in adjacent lanes are cut and eluted. Competitive inhibition by the end-specific antibodies to binding of $^{125}$I-labeled A β (1-40/1-42) to the RAGE receptor is determined in a number of ways: (1) different amounts (0-150 μg) of purified protein are immobilized on microtiter wells and incubated with 100 nM $^{125}$I-labeled A β (1-40/1-42); (2) different amounts (0-250 nM) of $^{125}$I-labeled A β (1-40/1-42) are incubated in microtiter wells pre-coated with 5 μg purified RAGE receptor; and (3) different amounts (0-500 μg/ml) of A β (1-40/1-42) are immobilized on microtiter wells and incubated with 50 nM $^{125}$I-labeled RAGE receptor. In each assay, the amount of ligand binding to the well in the presence of different amounts of antibody is determined by counting the amount of radioactivity in the wells with a gamma-scintillation counter.

To evaluate the efficacy of the different end-specific A β antibodies as inhibitors of Aβ-induced cellular oxidant stress, cultured mouse brain microvascular endothelial cells (Breitner et al., 1994) are incubated with 0.25 μM A β in the presence of different amounts of the antibodies, and cellular oxidant stress is assessed by measuring the dose-dependent generation of thiobarbituric acid-reactive substances using the TBARS assay as previously described (Dennery et al., 1990; Yan et al., 1996). In a parallel assay system (developed by Khoury et al., 1996), the inhibitory effects of the antibodies are tested on Aβ-induced production of oxygen-reactive species in N9 mouse microglial cells. N9 cells (5×10⁴ are incubated at 37° C. in the presence of different amounts of the antibodies in 50 μl PD-BSA (phosphate-buffered saline lacking divalent cation having 1 mg/ml BSA) containing 1 μM H₂DCF (2',7'-dichlorofluorescein diacetate), a dye that fluoresces upon oxidation (Wan et al., 1993) on muiltispot slides coated with Aβ peptides. At various time points, aliquots of the culture medium are taken and the fluorescence is measured in a fluorescence plate reader (Cytofluor II).

Effect on Interactions with Proteoglycans:

The vascular cell derived heparan sulfate proteoglycan, perlecan, has been identified in all amyloid deposits and is implicated in the earliest stages of inflammation-associated amyloid induction through high-affinity binding interactions with Aβ (Snow et al. 1989; 1995), Binding of perlecan to Aβ imparts secondary and tertiary amyloid structural features which suggest that molecules that interfere with the interaction may prevent or arrest amyloidogenesis.

Free end-specific Aβ antibodies made to peptides that correspond to the N-terminus of the peptide are evaluated for their ability to block the binding of perlecan to the perlecan binding site in the N-terminus region of Aβ (Snow et al., 1995). These evaluations are based on a solid-phase binding assay using perlecan isolated from cultured endothelial cells prepared from calf thoracic aortas as described in detail by (Snow et al. 1995). Polyvinyl micro-titer wells are coated with 100 μl of nitrocellulose solution and allowed to dry. Wells are then coated overnight at room temp with unlabeled perlecan to give 0.28 ug of bound perlecan per well, and blocked overnight at room temp with 200 μl of 5% non-fat dried milk.

Various quantities of $^{125}$I Aβ (7000 cpm/pM) diluted in 100 μl of TBS/0.05% Tween 20 (TBST) are added in triplicate to the wells and incubated for 2.5 h at room temp on an orbital shaker. At the end of the incubation period, free $^{125}$I A β is removed with six washes of TBST. Bound $^{125}$I is extracted in 100 μl 1N sodium hydroxide and "bound" versus "free" radioactivity is quantitated by liquid scintillation counting. Scatchard analysis is performed after incubating $^{125}$I-A β in the presence of increasing amounts of antibody.

Effects on Aβ Fibril Formation:

Amyloid fibril formation by the kinetically soluble peptides, such as Aβ 1-40, can be nucleated or "seeded" by peptides such as Aβ1-42 that include the critical C-terminal residues 41(Ile) and 42(Ala). The ability of C-terminus or N-terminus end-specific Aβ antibodies to block seed by Aβ 1-42 or to prevent aggregation of amyloid peptides is tested using standard aggregation assays (Wood et al., 1996). The Aβ 1-40 peptide is solubilized to 5 mg/ml in 1,1,1,3,3,3-hexafluoro-2-propanol. The peptide is concentrated to dryness and is resolubilized in phosphate-buffered saline (PBS), pH 7.4, to a final concentration of 230 μm. A solution of Aβ1-42 (20 μm) is stirred for 3 days and sonicated for 30 min to produce amyloid fibrils. Preaggregated Aβ 1-42 at 2 nM concentration is added to the supersaturated pH 7.4 incubation to seed aggregation of Aβ 1-40. Aggregate formation in the absence and in the presence of each Aβ end-specific antibody is determined by monitoring the turbidity of samples prepared in microtiter wells using a microtiter plate reader at 405 nm. The reaction is also monitored by thioflavin-T fluorescence as described by Wood et al. (1996). The ability of free-end-specific antibodies to promote disaggregation of amyloid peptide fibrils is tested by testing the displacement of VI-labeled amyloid aggregated peptides from a collagen matrix containing non-aggregated peptides coated onto 96-well microtiter-plastic-coated plates. In addition, the ability of free-end-specific-antibodies to protect neurons from Aβ-induced damage is assessed by the trypan blue exclusion method, intracellular calcium measurements, scanning and transmission electron microscopy and by confocal microscopy.

Animal models to establish the therapeutic potential of the Aβ antibodies

Animal models may be required to demonstrate the potential of antibody administration to slow down or prevent the development of AD-like pathology in the brain. Although AD is a uniquely human disease, a number of transgenic mice that overexpress human APP and PS1 have been developed. The correlative appearance of behavioral, biochemical, and pathological abnormalities reminiscent of Alzheimer's Disease in these transgenic mice provides the opportunity to explore the usefulness of agents to slow down or prevent the Aβ-induced pathophysiology of the disease.

The APP/PSI double transgenic model ((Holcomb et al, Nat Med 1998, 4:97-101)) has a particularly robust, reproducible phenotype which occurs very rapidly with first amyloid deposits and behavioral impairment detectable by 12 weeks of age. These factors combine to produce a model for rapid screening and evaluation of a drug candidate for Alzheimer's disease. Importantly, the phenotype of PS1/APP is consistent with several key features of human Alzheimer's disease and includes, for example, markers of oxidative stress, reactive gliosis, inflammation, neurodegeneration, abnormal neuronal growth, reorganization of cholinergic terminals, and the presence of hyperphosphorylated tau, an intermediate in tangle formation. Unlike many other models of cognitive impairment, PS1/APP has a selective "working memory" loss that is not accompanied by motor deficits.

A typical protocol for the evaluation of antibody in the APP/PS1 double transgenic mouse model for Alzheimer's disease is as follows: Treatments start at 5-6 weeks of age. Transgenic mice are randomized into 3 main groups (control and 2 doses of compound) with 10-12 animals per group. Each group is treated for up to 8 (before plaques deposition), 12 (when plaques start appearing) and 18-19 weeks of age (when amyloid burden is very pronounced), as shown above.

At each time point, the mice will be euthanized and perfused with saline or sucrose, brains will be harvested and hemispheres will be separated. One hemisphere will be fixed by immersion in paraformaldehyde, sectioned, and stained with Campbell-Switzer Alzheimer silver stain for plaque detection, or additional staining protocols. The other hemisphere will be snap frozen and then processed for ELISA testing, for the quantification of soluble and insoluble, 1-40 and 1-42, β-amyloid.

Prior to sacrifice, behavioral testing, such as the Y-maze, "place set" Morris water maze and trace conditioning can be performed.

REFERENCES

Andra, K. et al., "Expression of APP in transgenic mice: a comparison of neuron-specific promoters", *Neurobiol Aging* 17:183-190 (1996).

Barrow, C J et al., "Solution conformations and aggregational properties of synthetic amyloid beta-peptides of Alzheimer's Disease. Analysis of circular dichroism spectra", *J Mol Biol* 225:1075-1093 (1992).

Biocca, S et al., "Intracellular expression of anti-p21ras single chain Fv fragments inhibits meiotic maturation of xenopus oocytes", *Biochem Biophys Res Commun* 197: 422-427 (1993).

Biocca, S et al., "Intracellular immunization: Antibody targeting to subcellular compartments", *Trends in Cell Biol* 5:248-253 (1995).

Blacklow, N R et al., "Epidemiology of adenovirus-associated virus infection in a nursery population", *Am J Epidemiol* 88:368-378 (1968).

Breitner, J et al., "Inverse association of anti-inflammatory treatments and Alzheimer's Disease: initial results of a co-twin control study", *Neurology* 44:227-232 (1994).

Brinster, R L et al., "Somatic expression of herpes thymidine kinase in mice following injection of a fusion gene into eggs", *Cell* 27:223-231 (1981).

Burdick, D et al., "Assembly and aggregation properties of synthetic Alzheimer's A4/beta amyloid peptide analogs", *J Biol Chem* 267:546-564 (1992).

Busciglio, J et al., "Nucleic acidration of beta-amyloid in the secretory pathway in neuronal and nonneuronal cells *Proc Nat Acad Sci USA* 90:2092-2096 (1993).

Cai, X D et al., "Release of excess amyloid beta protein from a mutant aniyloid beta protein precursor", *Science* 259: 514-516 (1993).

Carter, B. J. In: *Handbook of Parvoviruses* ed., Tijssen P. L. (CRC Press, Boca Raton, Fla.) 2, 247-294 (1990).

Cattaneo, A et al., "Polymeric immunoglobin M is secreted by transfectants of non-lymphoid cells in the absence of immunoglobulin J chain", *EMBO J* 6:2753-2758 (1987).

Chartier-Harlin, M C et al., "Early-onset Alzheimer's Disease caused by mutations at codon 717 of the beta-amyloid precursor protein nucleic acid", *Nature* 353:844-846 (1991).

Citon, M et al., "Excessive production of amyloid beta-protein by peripheral cells of symptomatic and presymptomatic patients carrying the Swedish familial Alzheimer disease mutation", *Proc Nat Acad Sci USA* 91:11993-11997 (1994).

Clements, A et al., "Effects of the mutations Glu22 to Gln and Ala21 to Gly on the aggregation of a synthetic fragment of the Alzheimer's amyloid beta/A4 peptide", *Neurosci Lett* 161:17-20 (1993).

Dennery, P et al., "Effect of fatty acid profiles on the susceptibility of cultured rabbit tracheal epithelial cells to hyperoxic injury", *Am J Resp Cell Mol Biol* 3:137-144 (1990).

Du, B et al., "Efficient transduction of human neurons with an adeno-associated virus vector", *Nucleic acid Therapy* 3:254-261 (1996).

Dickson, D et al., "Alzheimer's Disease, A double-labeling immunohistochemical study of senile plaques", *Am J Pathol* 132:86-101 (1988).

Duan, L et al., "More convenient 13C-urea breath test modifications still meet the criteria for valid diagnosis of *Helicobacter pylori* infection", *Proc Nat Acad Sci USA* 91:5075-5079 (1994).

El Khoury, J et al., "Scavenger receptor-mediated adhesion of microglia to beta-amyloid fibrils", *Nature* 382:716-719 (1996).

Engvall, E et al., "Enzyme-linked immuuosorbent assay (ELISA). Quantitative assay of immunoglobulin G" *Immunochemistry* 8:871-874 (1971).

Esch, F S et al., "Cleavage of amyloid beta peptide during constitutive processing of its precursor", *Science* 248: 1122-1124 (1990).

Fabian, H et al., "Sythetic post-translationally modified human A beta peptide exhibits a markedly increased tendency to form beta-pleated sheets in vitro", *Eur J Biochem* 221:959-964 (1994).

Glenner, G G et al., "Alzheimer's Disease: initial report of the purification and characterization of a novel cerebrovascular amyloid protein", *Biochem Biophys Res Commun* 120: 885-890 (1984).

Goate, A et al., "Predisposing locus for Alzheimer's Disease on chromosome 21", *Lancet* 1:352-355 (1989).

Goate, A. et al., "Segregation of a missense mutation in the amyloid precursor protein gene with familial Alzheimer's Disease", *Nature* 349:704-706 (1991).

Golde, T E et al., "Processing of the amyloid protein precursor to potentially amyloidogenic derivatives", *Science* 255: 728-730 (1992).

Gordon, J W et al., "Nucleic acidic transformation of mouse embryos by microinjection of purified DNA", *Proc Nat Acad Sci (USA)* 77:7380-7384 (1980).

Gouras, G et al., "Expression of human APP in vitro and in vivo in rodent brain via adeno-associated virus (AAV) vectors", *Soc Neurosci Abst* 22:1661 (1996).

Gravina S A et al., "Amyloid beta protein (A beta) in Alzheimer's Disease brain. Biochemical and immunocytochemical analysis with antibodies specific for forms ending at A beta 40 or A beta 42(43)", *J Biol Chem* 270:(13): 7013-7016 (1995).

Griffiths et al., In: *Hybridoma Technology in Biosciences and Medicine*, ed. Springer, T. A. (Plenum New York). pp 103-105 (1985).

Haass, C et al., "The vascular H(+)-ATPase inhibitor bafilomycin A1 differentially affects proteolytic processing of mutant and wild-type beta-amyloid precursor protein", *J Biol Chem* 270:6186-6192 (1995).

Haass, C. et al., "Amyloid beta-peptide is produced by cultured cells during normal metabolism", *Nature* 359:322-325 (1992).

Halverson, K et al., "Molecular determinants of amyloid deposition in Alzheimer's Disease: conformational studies of synthetic beta-protein fragments", *Biochemistry* 29:2639-2664 (1990).

Harbers, K et al., "Microinjection of cloned retroviral genomes into mouse zygotes: integration and expression in the animal", *Nature* 293:540-542 (1981).

Hardy, J A et al., "Alzheimer's Disease: the amyloid cascade hypothesis", *Science* 256:184-185 (1992).

Harrington C R et al., "Charactersation of an epitope specific to the neuron-specific isoform of human enolase recognized by a monoclonal antibody raised against a synthetic peptide corresponding to the C-terminus of beta/A4-protein", *Biochim Biophys Acta* 1158 (2):120-128 (1993).

Hendriks, L et al., "Presenile dementia and cerebral haemorrhage linked to a mutation at codon 692 of the beta-amyloid precursor protein nucleic acid", *Nat Nucleic acidt* 1:218-221 (1992).

Higaki, J et al., "Inhibition of beta-amyloid formation identifies proteolytic precursors and subcellular site of catabolism", *Neuron* 14:651-659 (1995).

Howland, D S et al., "Mutant and native human beta-amyloid precursor proteins in transgenic mouse brain", *Neurobiol Aging* 16:685-699 (1995).

Hsiao, K, et al., "Correlative memory deficits, A beta elevation, and amyloid plaques in transgenic mice", *Science* 274:99-102 (1996).

Iwatsubo T et al., "Visualization of A beta 42(43) and A beta 40 in senile plaques with end-specific A beta monoclonals: evidence that an initially deposited species is A beta 42(43)", *Neuron* 13(1):45-53 (1994).

Jarrett, J T et al., "Seeding "one-dimensional crystallization" of amyloid: a pathogenic mechanism in Alzheimer's Disease and scrapie?", *Cell* 73:1055-1058 (1993a).

Jarrett, J T et al,, "The carboxy terminus of the beta amyloid protein is critical for the seeding of amyloid formation: implications for the pathonucleic acidsis of Alzheimer's Disease", *Biochemistry* 32:4693-4697 (1993b).

Kang, J et al., "The precursor of Alzheimer's Disease amyloid A4 protein resembles a cell-surface receptor", *Nature* 325: 733-736 (1987).

Kaplitt M G, et al., "Preproenkephalin promoter yields region-specific and long-term expression in adult brain after direct in vivo nucleic acid transfer via a defective herpes simplex viral vector", *Proc Nat Acad Sci USA* 91:8979-8983 (1994).

Kisilevsky, R et al., "Arresting amyloidosis in vivo using small-molecule anionic sulphonates or sulphates: implications for Alzheimer's Disease", *Nature Med* 1:143-148 (1995).

Kitaguchi, N et al., "Novel precursor of Alzheimer's Disease amyloid protein shows protease inhibitory activity", *Nature* 331:530-532 (1988).

Knops, J et al., "Cell-type and amyloid precursor protein-type specific inhibition of A beta release by bafilomycin A1, a selective inhibitor of vascular ATPases", *J Biol Chem* 270: 2419-2422 (1995).

Kohler et al., "Contituous cultures of fused cells secreting antibody of predefined specificity", *Nature* 256:495-496 (1975).

Konig, G et al., "Identification and differential expression of a novel alternative splice isoform of the beta A4 amyloid precursor protein (APP) mRNA in leukocytes and brain microglial cells", *J Biol Chem* 267:10804-10809 (1992).

Konig, G et al., "Development and characterization of a monoclonal antibody 369.2B specific for the carboxyl-terminus of the beta A4 peptide", *Ann NY Acad Sci* 777: 344-355 (1996).

Kotin, R M et al., "Site-specific integration by adeno-associated virus", *Proc Nat Acad Sci USA* 87:2211-2215 (1990).

Kotin, R M et al., "Mapping and direct visualization of a region-specific viral DNA integration site on chromosome 19q13-qter", *Genomics* 10:831-834 (1991).

Kotin, R M. et al., "Characterization of a preferred site on human chromosome 19q for integration of adeno-associated virus DNA by non-homologous recombination", *EMBO J* 11:5971-5078 (1992).

La Fauci, G et al., "Characterization of the 5'-end region and the first two exons of the beta-protein precursor nucleic acid", *Biochem Biophys Res Comm* 159:297-304 (1989).

Lahiri, D K, et al., "Promoter activity of the nucleic acid encoding the beta-amyloid precursor protein is up-regulated by growth factors, phorbol ester, retinoic acid and interleukin-1", *Brain Res Mol Brain Res* 32:233-240 (1995).

Luthman, H et al., "High efficiency polyoma DNA transfection of chloroquine treated cells", *Nucl Acids Res* 11:1295-1308 (1983).

Ma, J et al., "Amyloid-associated proteins alpha 1-antichymotrypsin and apolipoprotein E promote assembly of Alzheimer beta-protein into filaments", *Nature* 372:92-94 (1994).

Maniatis, T et al., *Molecular cloning: a laboratory manual.* (Cold Spriag Harbor Lab. Cold Spring Harbor N.Y.) (1989).

Marasco, W et al., "Design, intracellular expression, and activity of a human anti-human immunodeficiency virus type I gp120 single-chain antibody", *Proc Nat Acad Sci USA* 90:7889-7893 (1993).

Masters, C L et al., "Amyloid plaque core protein in Alzheimer disease and Down syndrome", *Proc Nat Acad Sci USA* 82:4245-4249 (1985).

Mhashilkar, A et al., "Inibition of HIV-1 Tat-mediated LTR transactivation and HIV-1 infection by anti-Tat single chain intrabodies", *EMBO J* 14:1542-1551 (1995).

Miller, D L et al., "Peptide compositions of the cerebrovascular and senile plaque core amyloid deposits of Alzheimer's Disease", *Arch Biochem Biophys* 301:41-52 (1993).

Mullan, M et al., "A pathogenic mutation for probable Alzheimer's Disease in the APP nucleic acid at the N-terminus of beta-amyloid", *Nat Nucleic acidt* 1:345-347 (1992).

Murphy, G M Jr. et al. "Development of a monoclonal antibody specific for the COOH-terminal of beta-amyloid 1-42 and its immunohistochemical reactivity in Alzheimer's Disease and related disorders *Am J Path* 144(5):1082-1088 (1994).

Murrell, J et al., "A mutation in the amyloid precursor protein associated with hereditary Alzheimer's Disease", *Science* 254:97-99 (1991).

Muzyzka, N, "Use of adeno-associated virus as a nucleic acidral transduction vector for mammalian cells", *Cuur Top Microbiol Immunol* 158(97):97-129 (1992).

Neve, R L et al., "Expression of the Alzheimer amyloid precursor nucleic acid trascripts in the human brain", *Neuron* 1:669-677 (1988).

Nishimoto, I et al., "Alzheimer amyloid protein precursor complexes with brain GTP-binding protein G(o)", *Nature* 362:75-79 (1993).

Orlandi et al., "Cloning immunoglobulin variable domains for expression by the polymerase chain reaction", *Proc Nat Acad Sci USA* 86:3833-3837 (1989).

Palmiter, R D et al., "Metallothionein-human GH fusion nucleic acids stimulate growth of mice", *Science* 222:809-814 (1983).

Pericak-Vance, M A et al., "Linkage studies in familial Alzheimer disease: evidence for chromosome 19 linkage", *Am J Hum Nucleic acidt* 48:1034-1050 (1 991).

Piccioli, P et al., "Neuroantibodies: molecular cloning of a monoclonal antibody against substance P for expression in the central nervous system", *Proc Nat Acad Sci USA* 88:5611-5615 (1991).

Piccioli, P et al., "Neuroantibodies: ectopic expression of a recombinant anti-substance P antibody in the central nervous system of transgenic mice", *Neuron* 15:373-384 (1995).

Pleasure, S J et al., "NTera 2 cells: a human cell line which displays characteristics expected of a human committed neuronal progenitor cell", *J Neurosci Res.* 35, 585-602 (1993).

Ponte, P. et al., "A new A4 amyloid mRNA contains a domain homologous to serine proteinase inhibitors", *Nature* 331: 525-527 (1988).

Richardson, J H et al., "Phenotypic knockout of the high-affinity human interleukin 2 receptor by intracellular single-chain antibodies against the alpha subunit of the receptor", *Proc Nat Acad Sci USA* 92:3137-3141 (1995).

Roch, J M et al., "Biologically active domain of the secreted form of the amyloid beta/A4 protein precursor", Ann NY Aca Sci. 695:149-157 (1993).

Roher, A E; et al., "Morphological and biochemical analyses of amyloid plaque core proteins purified from Alzheimer disease brain tissue", *J Neurochem* 61:1916-1926 (1993).

Rumble, B et al., "Amyloid A4 protein and its precursor in Down's syndrome and Alzheimner's Disease", *N Engl J Med* 320:1446-1452 (1989).

Theo, T C et al., "Spatial resolution of fodrin proteolysis in postischemic brain", J Biol Chem 268, 25239-25243 (1993).

Theo, T C et al., "Spatial resolution of the primary beta-amyloidogenic process induced in postischemic hippocampus", *J Biol Chem* 269:15253-15257 (1994).

Saitoh, T et al., In: *Amyloid Protein Precursor in Development, Aging and Alzheimer's Disease*, C. L. Masters, ed. (Heidelberg, Germany, Springer-Verlag (1994).

Salbaum, J M, et al., "The promoter of Alzheimer's Disease amyloid A4 precursor nucleic acid", *EMBO J* 7:2807-2813 (1988).

Samulski, R J et al., "A recombinant plasmid from which an infectious adeno-associated virus genome can be excised in vitro and its use to study viral replication", *J Virol* 61:3096-3101 (1987).

Samulski, R J et al., "Helper-free stocks of recombinant adeno-associated viruses: normal integration does not require viral nucleic acid expression", *J Virol* 63:3822-3828 (1989).

Samulski, R. J et al., "Targeted integration of adeno-associated virus (AAV) into human chromosome 19", *EMBO J* 10:3941-3850 (1991).

Schellenberg, G. D. et al., "Nucleic acidtic linkage evidence for a familial Alzheimer's Disease locus on chromosome 14" *Science* 258:668-671 (1992).

Schehr, R S, "Therapeutic approaches to Alzheimer's Disease. An informal survey of promising drug discovery strategies", *Biotechology* 12:140-144 (1994).

Schubert, D et al., "The regulation of amyloid beta protein precursor secretion and its modulatory role in cell adhesion", *Neuron* 3:689-694 (1989).

Seubert, P et al., "Isolation and quantification of soluble Alzheimer's beta-peptide from biological fluids", *Nature* 359:325-327 (1992).

Shoji, M et al., "Production of the Alzheimer amyloid beta protein by normal proteolytic processing", *Science* 258: 126-129 (1992), Sisodia, S et al., "Role of the beta-amyloid protein in Alzheimer's Disease", *FASEB J* 366-369 (1995).

Sisodia, S et al., "Beta-amyloid precursor protein cleavage by a membrane-bound protease", *Proc Nat Acad Sci USA* 89:6075-6079 (1992).

Snow, A D et al., "Differential binding of vascular cell-derived proteoglycans (perlecan, biglycan, decorin, and versican) to the beta-amyloid protein of Alzheimer's Disease", *Arch Biochem Bioyhys* 320:84-95 (1995).

Snow, A D et al, "Proteoglyeans in the pathonucleic acidsis of Alzheimer's Disease and other amyloidoses", *Neurobiol Aging* 10(5):481-97 (1989).

Solomon B et al., "Disaggregation of Alzheimer beta-amyloid by site-directed mAb", *Proc Nat Acad Sci USA* 94:4109-4112 (1997).

Steward, T A et al., "Human beta-globin nucleic acid sequences injected into mouse eggs, retad in adults, and transmitted to progeny", *Science* 217:1046-1048 (1982).

Suzuki, N et al., "An increased percentage of long amyloid beta protein secreted by familial amyloid beta protein precursor (beta APP717) mutants", *Science* 264:1336-1340 (1994).

Tagliavini, F et al, "Preamyloid deposits in the cerebral cortex of patients with Alzheimer's Disease and nondemented individuals", *Neurosci Lett* 93:191-196 (1988).

Tanzi, R E et al., "Protease inhibitor domain encoded by an amyloid protein precursor mRNA associated with Alzheimer's Disease", *Nature* 331:528-530 (1988).

Tanzi, R E et al., "Assessment of amyloid beta-protein precursor nucleic acid mutations in a large set of familial and sporadic Alzheimer disease cases", *Am J Hum Nucleic acidt* 51:273-282 (1992).

Tomiyama et al., "Rifampicin prevemts the aggregation and neurotoxicity of amyloid beta protein in vitro", *Biochem Biophys Res Commun* 204:76-83 (1994).

Van Broeckoven, C et al,, "Failure of familial Alzheimer's Disease to segregate with the A4-amyloid nucleic acid in several European families", *Nature* 329:153-155 (1987).

Wagner, E F et al., "The human beta-globin nucleic acid and a functional viral thymidine kinase nucleic acid in developing mice", *Proc Nat Acad Sci USA* 78:5016-5020 (1981).

Wan, C P et al., "An automated micro-fluorometric assay for monitoring oxidative burst activity of phagocytes", *J Immunol Meth* 159:131-138 (1993).

Ward, E S et al., "Binding activities of a repertoire of single immunoglobulin variable domains secreted from *Escherichia coli*", *Nature* 341:544-546 (1999).

Weidemann, A et al., "Identification, bionucleic acidsis, and localization of precursors of Alzheimer's Disease A4 amyloid protein", *Cell* 57:115-126 (1989).

Wertkin, A M et al., "Human neurons derived from a teratocarcinoma cell line express solely the 695-amino acid amyloid precursor protein and produce intracellular beta-amyloid or A4 peptides", *Proc Nat Acad Sci USA* 90:9513-9517 (1993).

Wigler, M. et al., "DNA-mediated transfer of the adenine phosphoribosyltransferase locus into mammalian cells", *Proc Nat Acad Sci USA* 765:1373-1376 (1979).

Wirak et al., "Regulatory region of human amyloid precursor protein (APP) nucleic acid promotes neuron-specific nucleic acid expression in the CNS of transgenic mice", *EMBO S* 10:289-296 (1991).

Wisniewski, T et al., "Acceleration of Alzheimer's fibril formation by apolipoprotein E in vitro", *Am J Pathol* 145:1030-1035 (1994).

Wisniewski, T et al., "Peptides homologous to the amyloid protein of Alzheimer's Disease containing a glutae for gluac acid substitutioni have accelerated amyloid fibril formation", *Biochem Biophys Res Commun* 179:1247-1254 (1991).

Wood, S J et al., "Selective inhibition of Abeta fibril formation", *J Biol Chem* 271:4086-4092 (1996).

Wu, P et al., "Differential neuropeptide Y nucleic acid expression in post-mitotic versus dividing neuroblastoma cells driven by an adeno-associated virus vector", *Brain Res Mol Brain Res* 24:27-33 (1994).

Wu, P et al., "Sendai virosomal infusion of an adeno-associated virus-derived construct containing neuropeptide Y into primary rat brain cultures", *Neurosci Lett* 190:73-76 (1995).

Yamaguchi, H et al., "Electron micrograph of diffuse plaques. Initial stage of senile plaque formation in the Alzheimer braun", *Am J Pathol* 135:593-597 (1989).

Yamaguchi, H et al., "Ultrastructural localization of Alzheimer amyloid beta4A protein precursor in the cytoplasm of neurons and senile plaque-associated astrocytes", *Acta Neuropathol* 82:13-20 (1992).

Yan, S D et al., "RAGE and amyloid-beta peptide neurotoxicity in Alzheimer's disease", *Nature* 382:685-691 (1996).

Yankner, B A et al., "Seminars in medicine of the Beth Israel Hospital, Boston. beta-Amyloid and the pathonucleic acidsis of Alzheimer's Disease", *N Eng J Med* 325:1849-1857 (1991).

Zhu, N et al., "Systemic nucleic acid expression after intravenous DNA delivery into adult mice", *Science* 261:209-211 (1993)

---

What is claimed is:

1. A method for inhibiting accumulation of amyloid β peptide in the brain of a patient suffering from Alzheimer's disease, comprising contacting in vivo soluble amyloid β peptide in the cerebrospinal fluid of said patient with an exogenous free-end specific antibody which is targeted to a free C-terminus of amyloid β peptide Aβ1-40, to inhibit the accumulation of said amyloid β peptide in the brain of said patient.

2. The method of claim 1, wherein the antibody is a monoclonal antibody, a humanized antibody, a chimeric antibody, a scFv antibody or a F(ab), or fragment thereof.

3. The method of claim 1 wherein said exogenous free-end specific antibody is stably expressed in neuronal cells in the brain.

4. A method for inhibiting the neurotoxicity of amyloid β peptide in a patient suffering from Alzheimer's disease, comprising contacting in vivo soluble amyloid β peptide in the cerebrospinal fluid of said patient with an exogenous free-end specific antibody which is targeted to a free C-terminus of amyloid β peptide Aβ1-40, to inhibit the neurotoxicity of amyloid β peptide in said patient.

5. The method of claim 4, wherein the antibody is a monoclonal antibody, a humanized antibody, a chimeric antibody, a scFv antibody or a F(ab), or fragment thereof.

6. The method of claim 4 wherein said exogenous free-end specific antibody is stably expressed in neuronal cells in the brain.

7. A method of forming a complex, said method comprising:
providing to the cerebrospinal fluid of an individual, an agent that is a monoclonal antibody, humanized antibody, chimeric antibody, scFv antibody, F(ab) antibody, or a fragment of the foregoing types of antibodies, which agent specifically binds to an epitope within residues 34-40 of an amyloid β-peptide and which binds said amyloid β-peptide but does not significantly bind amyloid precursor protein,
to form in said cerebrospinal fluid a complex comprising said agent and said amyloid β-peptide.

8. The method of claim 7, wherein said agent is a humanized antibody or fragment thereof.

9. The method of claim 7, wherein said agent is a chimeric antibody or fragment thereof.

10. The method of claim 7 wherein said individual is an individual suffering from Alzheimer's disease or having a predisposition to develop Alzheimer's disease.

11. The method of claim 10 wherein said complex comprising said agent and said amyloid β-peptide is a soluble complex.

12. The method of claim 7 wherein said complex comprising said agent and said amyloid β-peptide is a soluble complex.

13. The method of claim 7 wherein said agent is stably expressed in neuronal cells in the brain.

14. A method for reducing the quantity of amyloid β-peptide in the cerebrospinal fluid of a patient suffering from Alzheimer's disease which comprises contacting said amyloid β-peptide in said cerebrospinal fluid of said patient with a monoclonal antibody, humanized antibody, chimeric antibody, scFv antibody, F(ab) antibody, or a fragment of the foregoing types of antibodies, that specifically binds to an epitope within residues 34-40 of said amyloid β-peptide and which binds said amyloid β-peptide but does not significantly bind amyloid precursor protein.

15. The method of claim 14, wherein said antibody is a humanized antibody or fragment thereof.

16. The method of claim 14, wherein said antibody is a chimeric antibody or fragment thereof.

17. The method of claim 14 wherein said antibody binds amyloid β-peptide that is soluble in the cerebrospinal fluid of said patient.

18. The method of claim 14 wherein said monoclonal antibody, humanized antibody, chimeric antibody, scFv antibody, F(ab) antibody, or fragment of the foregoing types of antibodies is stably expressed in neuronal cells in the brain.

19. A method for inhibiting the accumulation of amyloid β-peptide in a patient suffering from Alzheimer's disease which comprises contacting said amyloid β-peptide in the cerebrospinal fluid of said patient in vivo with a monoclonal antibody, humanized antibody, chimeric antibody, scFv antibody, F(ab) antibody, or a fragment of the foregoing types of antibodies, that specifically binds to an epitope within residues 34-40 of said amyloid β-peptide and which binds said amyloid β-peptide but does not significantly bind amyloid precursor protein.

20. The method of claim 19, wherein said antibody is a humanized antibody or fragment thereof.

21. The method of claim 19, wherein said antibody is a chimeric antibody or fragment thereof.

22. The method of claim 19 wherein said antibody binds amyloid β-peptide that is soluble in the cerebrospinal fluid of said patient.

23. The method of claim 19 wherein said monoclonal antibody, humanized antibody, chimeric antibody, scFv antibody, F(ab) antibody, or fragment of the foregoing types of antibodies is stably expressed in neuronal cells in the brain.

* * * * *

SEQUENCE LISTING

```
<160> NUMBER OF SEQ ID NOS: 17

<210> SEQ ID NO 1
<211> LENGTH: 59
<212> TYPE: PRT
<213> ORGANISM: Homo sapiens

<400> SEQUENCE: 1

Glu Val Lys Met Asp Ala Glu Phe Arg His Asp Ser Gly Tyr Glu Val
1               5                   10                  15

His His Gln Lys Leu Val Phe Phe Ala Glu Asp Val Gly Ser Asn Lys
            20                  25                  30

Gly Ala Ile Ile Gly Leu Met Val Gly Gly Val Val Ile Ala Thr Val
        35                  40                  45

Ile Val Ile Thr Leu Val Met Leu Lys Lys Lys
    50                  55

<210> SEQ ID NO 2
<211> LENGTH: 6
<212> TYPE: PRT
<213> ORGANISM: Homo sapiens

<400> SEQUENCE: 2
```

```
Asp Ala Glu Phe Arg Cys
1               5

<210> SEQ ID NO 3
<211> LENGTH: 8
<212> TYPE: PRT
<213> ORGANISM: Homo sapiens

<400> SEQUENCE: 3

Asp Ala Glu Phe Arg His Asp Cys
1               5

<210> SEQ ID NO 4
<211> LENGTH: 8
<212> TYPE: PRT
<213> ORGANISM: Homo sapiens

<400> SEQUENCE: 4

Cys Leu Met Val Gly Gly Val Val
1               5

<210> SEQ ID NO 5
<211> LENGTH: 8
<212> TYPE: PRT
<213> ORGANISM: Homo sapiens

<400> SEQUENCE: 5

Cys Val Gly Gly Val Val Ile Ala
1               5

<210> SEQ ID NO 6
<211> LENGTH: 6
<212> TYPE: PRT
<213> ORGANISM: Homo sapiens

<400> SEQUENCE: 6

Asp Ala Glu Phe Arg His
1               5

<210> SEQ ID NO 7
<211> LENGTH: 13
<212> TYPE: PRT
<213> ORGANISM: Homo sapiens

<400> SEQUENCE: 7

Glu Ile Ser Glu Val Lys Met Asp Ala Glu Phe Arg His
1               5                   10

<210> SEQ ID NO 8
<211> LENGTH: 4
<212> TYPE: PRT
<213> ORGANISM: Homo sapiens

<400> SEQUENCE: 8

Glu Phe Arg His
1

<210> SEQ ID NO 9
<211> LENGTH: 6
<212> TYPE: PRT
<213> ORGANISM: Homo sapiens

<400> SEQUENCE: 9

Glu Val His His Gln Cys
1               5
```

<210> SEQ ID NO 10
<211> LENGTH: 12
<212> TYPE: PRT
<213> ORGANISM: Homo sapiens

<400> SEQUENCE: 10

Phe Arg His Asp Ser Gly Tyr Glu Val His His Gln
1               5                   10

<210> SEQ ID NO 11
<211> LENGTH: 8
<212> TYPE: PRT
<213> ORGANISM: Homo sapiens

<400> SEQUENCE: 11

Cys Gly Gly Val Val Ile Ala Thr
1               5

<210> SEQ ID NO 12
<211> LENGTH: 13
<212> TYPE: PRT
<213> ORGANISM: Homo sapiens

<400> SEQUENCE: 12

Asn Lys Gly Ala Ile Gly Leu Met Val Gly Gly Val Val
1               5                   10

<210> SEQ ID NO 13
<211> LENGTH: 14
<212> TYPE: PRT
<213> ORGANISM: Homo sapiens

<400> SEQUENCE: 13

Ala Ile Ile Gly Leu Met Val Gly Gly Val Val Ile Ala Thr
1               5                   10

<210> SEQ ID NO 14
<211> LENGTH: 5
<212> TYPE: PRT
<213> ORGANISM: Homo sapiens

<400> SEQUENCE: 14

Asp Ala Glu Phe Arg
1               5

<210> SEQ ID NO 15
<211> LENGTH: 42
<212> TYPE: PRT
<213> ORGANISM: Homo sapiens

<400> SEQUENCE: 15

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 16
<211> LENGTH: 7
<212> TYPE: PRT
<213> ORGANISM: Homo sapiens
<220> FEATURE:
<221> NAME/KEY: MISC_FEATURE
<222> LOCATION: (6)..(6)

```
<223> OTHER INFORMATION: Xaa is aminohexanoate
<220> FEATURE:
<221> NAME/KEY: MISC_FEATURE
<222> LOCATION: (7)..(7)
<223> OTHER INFORMATION: Xaa is Cys-amide

<400> SEQUENCE: 16

Asp Ala Glu Phe Arg Xaa Xaa
1               5

<210> SEQ ID NO 17
<211> LENGTH: 10
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa is acetyl-Glu

<400> SEQUENCE: 17

Xaa Val Lys Met Asp Ala Glu Phe Arg His
1               5                   10
```